(12) United States Patent
Itai et al.

(10) Patent No.: US 7,998,992 B2
(45) Date of Patent: Aug. 16, 2011

(54) OXAZOLIDINONE DERIVATIVE HAVING INHIBITORY ACTIVITY ON 11β-HYDROXYSTEROID DEHYDROGENASE TYPE 1

(75) Inventors: Akiko Itai, Tokyo (JP); Susumu Muto, Tokyo (JP); Ryuko Tokuyama, Tokyo (JP); Hiroshi Fukasawa, Tokyo (JP); Takeshi Yanase, Tokyo (JP)

(73) Assignees: Institute of Medicinal Molecular Design, Inc., Tokyo (JP); Shionogi & Co., Ltd., Osaka (JP)

( * ) Notice: Subject to any disclaimer, the term of this patent is extended or adjusted under 35 U.S.C. 154(b) by 0 days.

(21) Appl. No.: 12/594,093

(22) PCT Filed: Mar. 27, 2008

(86) PCT No.: PCT/JP2008/055827
§ 371 (c)(1),
(2), (4) Date: Sep. 30, 2009

(87) PCT Pub. No.: WO2008/120655
PCT Pub. Date: Oct. 9, 2008

(65) Prior Publication Data
US 2010/0113448 A1 May 6, 2010

(30) Foreign Application Priority Data
Mar. 30, 2007 (JP) .................................. 2007-091023

(51) Int. Cl.
| | |
|---|---|
| A01N 43/76 | (2006.01) |
| A01N 43/36 | (2006.01) |
| A61K 31/42 | (2006.01) |
| A61K 31/535 | (2006.01) |
| A61K 31/40 | (2006.01) |
| C07D 263/00 | (2006.01) |

(52) U.S. Cl. ..................... 514/376; 514/236.8; 514/424; 548/229

(58) Field of Classification Search .................. 514/376, 514/236.8, 424; 548/229
See application file for complete search history.

(56) References Cited

U.S. PATENT DOCUMENTS

| | | | | |
|---|---|---|---|---|
| 3,062,828 | A * | 11/1962 | Lunsford | 548/232 |
| 4,066,628 | A | 1/1978 | Ashida et al. | |
| 4,146,638 | A | 3/1979 | Renth et al. | |
| 4,602,093 | A | 7/1986 | Baldwin et al. | |
| 4,806,655 | A | 2/1989 | Wagnon et al. | |
| 5,480,899 | A * | 1/1996 | Yano et al. | 514/376 |
| 5,488,064 | A | 1/1996 | Sher | |
| 5,521,202 | A * | 5/1996 | Yano et al. | 514/369 |
| 5,606,069 | A | 2/1997 | Epstein et al. | |
| 5,827,857 | A | 10/1998 | Riedl et al. | |
| 5,843,975 | A | 12/1998 | Jegham et al. | |
| 2004/0242660 | A1 | 12/2004 | Straub et al. | |
| 2008/0306070 | A1 | 12/2008 | Perzborn et al. | |

FOREIGN PATENT DOCUMENTS

| | | |
|---|---|---|
| DE | 2109651 | 9/1971 |
| DE | 0153682 | 1/1982 |
| EP | 0064294 | 11/1982 |
| EP | 0251938 | 11/1991 |
| EP | 0645387 | 3/1995 |
| EP | 0605729 | 7/2000 |
| EP | 1261606 | 12/2002 |
| EP | 1526132 | 4/2005 |
| EP | 1251128 | 12/2006 |
| EP | 1852425 | 11/2007 |
| EP | 1864971 | 12/2007 |
| EP | 1894919 | 3/2008 |
| EP | 1953145 | 8/2008 |
| EP | 2006286 | 12/2008 |
| GB | 938424 | 10/1963 |
| JP | 49-20768 | 5/1974 |
| JP | 05-148247 | 6/1993 |
| JP | 11-035534 | 2/1999 |
| JP | 2000-136186 | 5/2000 |
| JP | 2000-290265 | 10/2000 |
| JP | 2001-055383 | 2/2001 |
| WO | 99/03846 | 1/1999 |
| WO | 99/64417 | 12/1999 |
| WO | 02/072542 | 9/2002 |
| WO | 2004/069244 | 8/2004 |

(Continued)

OTHER PUBLICATIONS

Chapman et al. Neurochem. Res. 2008, vol. 33, pp. 624-636.*

(Continued)

*Primary Examiner* — Sreeni Padmanabhan
*Assistant Examiner* — Samira Jean-Louis
(74) *Attorney, Agent, or Firm* — Hamre, Schumann, Mueller & Larson, P.C.

(57) ABSTRACT

Disclosed is a compound which is useful as an 11β-hydroxysteroid dehydrogenase type 1 inhibitor.
A compound represented by the formula:

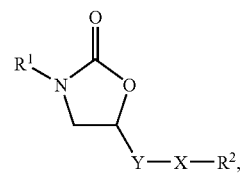

its pharmaceutically acceptable salt, or a solvate thereof,
wherein $R^1$ is optionally substituted cycloalkyl, optionally substituted cycloalkylalkyl, optionally substituted heterocycle or optionally substituted heterocyclealkyl,
X is —O—, —$NR^3$—, —$NR^3C(=O)$— or —$NR^3S(=O)_2$—,
$R^2$ is optionally substituted aryl, optionally substituted arylalkyl, optionally substituted heteroaryl or optionally substituted heteroarylalkyl,
$R^3$ is hydrogen or optionally substituted alkyl.

4 Claims, No Drawings

FOREIGN PATENT DOCUMENTS

| WO | 2004/069832 | 8/2004 |
|---|---|---|
| WO | 2005/108360 | 11/2005 |
| WO | 2005/108361 | 11/2005 |
| WO | 2006/124490 | 11/2006 |
| WO | 2007/118185 | 10/2007 |

OTHER PUBLICATIONS

Vippagunta et al. Advanced Drug Delivery Reviews. 2001, vol. 28, pp. 3-26.*

Tomkin et al. Proceedings of the Nutrition Society, 1991, vol. 50, pp. 583-589.*

Stewart, "11 β-Hydroxysteroid dehydrogenase: implications for clinical medicine", Clinical Molecular Endocrinology, 1996, pp. 493-499.

Kotelevtsev et al., "11 β-Hydroxysteroid dehydrogenase type 1 knockout mice show attenuated glucocorticoid-inducible responses and resist hyperglycemia on obesity or stress", Proc. Natl. Acad. Sci. USA, vol. 94, Dec. 1997, pp. 14924-14929.

Walker et al., "Carbenoxolone Increases Hepatic Insulin Sensitivity in Man: A Novel Role for 11-Oxosteroid Reductase in Enhancing Glucocorticoid Receptor Activation", Journal of Clinical Endocrinology and Metabolism, vol. 80, No. 11, 1995, pp. 3155-3159.

Bujalska et al., "Does central obesity reflect 'Cushing's disease of the omentum'?", The Lancet, vol. 349, Apr. 26, 1997, pp. 1210-1213.

Ohno et al., "Synthesis and Structure-Activity Relationship of 4-Substituted Benzoic Acids and their Inhibitory Effect on the Biosynthesis of Fatty Acids and Sterols", Arc. Pharm. Chem. Life Sci., vol. 338, 2005, pp. 147-158.

Rastogi et al.. "Solid phase synthesis of 3,5-disubstituted oxazolidin-2-ones", Tetrahedron Letters 43, 2002, pp. 8327-8330.

Maier et al., "Efficient high-performance liquid chromatographic enantioseparation of five-membered aryl-substituted lactones and cyclic carbamates on a (R,R)-diaminodihydroethanoanthracene-derived chiral stationary phase," Journal of Chromatography A, vol. 740, 1996, pp. 11-19.

Žilić et al., "Studies in the Formation of Poly(oxazolidone)s. III. Catalysis and Kinetics of the Model Oxazolidone Formation from Cyclohexyl Isocyanate and Phenylglycidyl Ether", Journal of Polymer Science: Part A: Polymer Chemistry, vol. 27, 1989, pp. 1843-1851.

Cardillo et al., "An Efficient Synthesis of (R)-(+)- and (S)-(−)-Propranolol from Resolved 5-Iodomethyloxazolidin-2-ones", Tetrahedron, vol. 43, No. 11, 1987 pp. 2505-2512.

Baldwin et al., "$\beta_1$-Selective Adrenoceptor Antagonists: Examples of the 2-[4-[3-(Substituted amino)-2-hydroxypropoxy]phenyl]imidazole Class. 2", Journal of Medicinal Chemistry, vol. 29, No. 6, 1986, pp. 1065-1080.

Kordomenos et al., "Oxazolidone Coatings Part 1: Synthesis and Structure", Journal of Coatings Technology, vol. 55, No. 700, May 1983, pp. 49-57.

Kordomenos et al., "Thermal Stability of Isocyanate-Based Polymers. 1. Kinetics of the Thermal Dissociation of Urethane, Oxazolidone, and Isocyanurate Groups", Macromolecules, vol. 14, No. 5, 1981, pp. 1434-1437.

Gulbins et al., "Synthese von substituierten Oxazolidonen-(2)", Chemische Berichte, Jahrg. 93, 1960, pp. 1975-1982.

Lunsford et al., "5-Aryloxymethy1-2-oxazolidinones", Journal of the American Chemical Society, vol. 82, Mar. 5, 1960, pp. 1166-1171.

Yeh et al., "Discovery of orally active butyrolactam 11β-HSD1 inhibitors", Bioorganic & Medicinal Chemistry Letters 16, 2006, pp. 5555-5560.

Mai et al., "Synthesis and biochemical evaluation of (R)-5-acyloxymethyl- and (S)-5-acylaminomethyl-3-(1H-pyrrol-1-yl)-2-oxazolidinones as new anti-monoamine oxidase (anti-MAO) agents," ARKIVOC, 2004, pp. 32-43.

Pazdro et al., "N-Mannich Bases of Some 5-Aryloxymethyl-2-oxazolidones", Dissertationes Pharmaceuticae et Pharmacologicae, 1970, pp. 297-303.

Landini et al., "S,S-Dimethyl Dithiocarbonate as a Valuable Starting Material for the Synthesis of 5-Substituted Oxazolidinones Under Solid-Liquid Phase Transfer Catalysis (SL-PTC) Conditions", Letters in Organic Chemistry, vol. 3, No. 11, 2006, pp. 836-841.

Anumula et al., "Synthesis of new oxazolidinonyl/oxazolidinyl carbazole derivatives for β-blocking activity," Heterocyclic Communications, 2007, vol. 13, No. 5, pp. 315-322.

* cited by examiner

OXAZOLIDINONE DERIVATIVE HAVING INHIBITORY ACTIVITY ON 11β-HYDROXYSTEROID DEHYDROGENASE TYPE 1

FIELD OF THE INVENTION

The present invention relates to a pharmaceutically useful compound having inhibitory activity on 11β-hydroxysteroid dehydrogenase type 1 (hereinafter, referred to as 11β-HSD-1).

BACKGROUND ART

11β-HSD-1 is an enzyme that converts 11β-dehydrosteroid, which is inactive steroid, into an active steroid, and is considered to have great significance in biological basal metabolism (Non-patent document 1). Also, an 11β-HSD-1 knockout mouse has resistance to hyperglycemia induced by obesity, stress and the like (Non-patent document 2). Also in human, a similar phenomenon was observed when carbenoxolone which is an 11β-HSD-1 inhibitor was administered (Non-patent document 3).

These facts suggest the possibility of a selective inhibitor of this enzyme as a therapeutic agent in insulin independent diabetes and obesity (Non-patent document 4).

Patent document 1 discloses a pyrano[2,3-d]pyrimidine derivative as a compound useful as a therapeutic agent for diabetes.

Patent document 2 discloses a thiazolidine derivative as a compound useful as a therapeutic agent for diabetes.

Patent document 3 discloses a derivative in which 3-position of oxazolidinone is substituted with arylalkyl as a compound useful as a herbicide.

Non-patent document 5 and Patent document 11 disclose a derivative in which 3-position of oxazolidinone is substituted with arylalkyl, as a compound useful as a cholesterol-lowering agent.

Patent document 4, Patent document 6 and Patent document 15 disclose a derivative in which 3-position of oxazolidinone is substituted with arylalkyl as a compound useful as a therapeutic agent for thromboembolism.

Non-patent document 6 discloses a solid-phase synthesis method of a derivative in which 3-position of oxazolidinone is substituted with arylalkyl.

Patent document 5 discloses a derivative in which 3-position of oxazolidinone is substituted with arylalkyl as a compound useful as a NMDA receptor antagonist.

Patent document 7 discloses a derivative in which 3-position of oxazolidinone is substituted with arylalkyl as a method of producing oxazolidone.

Patent documents 8, 9 and 10 disclose a derivative in which 3-position of oxazolidinone is substituted with arylalkyl as an intermediate of a compound useful as a therapeutic agent for diabetes.

Non-patent document 7, Patent document 13, Patent document 14 and Patent document 18 disclose a derivative in which 3-position of oxazolidinone is substituted with arylalkyl as a compound useful for an antihypertensive.

Patent document 12 discloses a derivative in which 3-position of oxazolidinone is substituted with arylalkyl as a compound useful for a cardiac stimulant.

Non-patent document 8, Non-patent document 11, Non-patent document 12, Patent document 16 and Non-patent document 13 disclose a synthesis method of a derivative in which 3-position of oxazolidinone is substituted with cyclohexyl.

Non-patent document 9 and Patent document 19 disclose a synthesis method of a derivative in which 3-position of oxazolidinone is substituted with arylalkyl.

Non-patent document 10 discloses a derivative in which 3-position of oxazolidinone is substituted with arylalkyl as a compound useful as a therapeutic agent for angina pectoris.

Patent document 17 discloses a derivative in which 3-position of oxazolidinone is substituted with arylalkyl as a compound useful as a therapeutic agent for hypotension.

Patent document 20 and Non-patent document 14 disclose a derivative in which 3-position of oxazolidinone is substituted with arylalkyl and cyclohexyl as a compound useful as a muscle relaxant.

Non-patent document 15 and Patent document 21 disclose a pyrrolidine-2-one derivative having 11β-HSD-1 inhibiting activity, but they fail to disclose an oxazolidinone derivative such as the present compound.

[Non-patent document 1] Clin. Endocrinol, 1996, vol. 44, p. 493
[Non-patent document 2] Proc. Nat. Acad. Sci. USA, 1997, vol. 94, p. 14924
[Non-patent document 3] J. Clin. Endocrinol. Metab., 1995, vol. 80, p. 3155
[Non-patent document 4] Lancet, 1997, vol. 349, p. 1210
[Non-patent document 5] Archiv der Pharmazie, 2005, vol. 338, No. 4, p. 147
[Non-patent document 6] Tetrahedron Letters, 2002, vol. 43, No. 46, 8327
[Non-patent document 7] Journal of Chromatography, A, 1996, vol. 740, No. 1, p. 11
[Non-patent document 8] Journal of Polymer Science, Part A, 1989, vol. 27, No. 6, p. 1843
[Non-patent document 9] Tetrahedron, 1987, vol. 43, No. 11, p. 2505
[Non-patent document 10] Journal of Medicinal Chemistry, 1986, vol. 29, No. 6, p. 1065
[Non-patent document 11] Journal of Coatings Technology, 1983, vol. 55, No. 700, p. 49
[Non-patent document 12] Macromolecules, 1981, vol. 14, No. 5, p. 1434
[Non-patent document 13] Chemische Berichte, 1960, vol. 93, p. 1975
[Non-patent document 14] Journal of the American Chemical Society, 1960, vol. 82, p. 1166
[Non-patent document 15] Bioorganic & Medicinal Chemistry Letters, 16 (2006), p. 5555
[Patent document 1] WO06/124490
[Patent document 2] WO94/022857
[Patent document 3] WO06/090792
[Patent document 4] WO03/000256
[Patent document 5] WO02/072542
[Patent document 6] WO01/047919
[Patent document 7] JP2001-055383
[Patent document 8] JP11-035534
[Patent document 9] U.S. Pat. No. 5,488,064
[Patent document 10] U.S. Pat. No. 5,606,069
[Patent document 11] WO93/022298
[Patent document 12] JP05-148247
[Patent document 13] U.S. Pat. No. 4,602,093
[Patent document 14] EP64294
[Patent document 15] DD153682
[Patent document 16] U.S. Pat. No. 4,066,628
[Patent document 17] DE2606140
[Patent document 18] JP49-020768
[Patent document 19] GB938424
[Patent document 20] U.S. Pat. No. 3,062,828
[Patent document 21] WO2007118185

DISCLOSURE OF INVENTION

Problems to be Solved by the Invention

The present invention provides a useful 11β-hydroxysteroid dehydrogenase type 1 inhibitor.

The present invention provides:

(1)
A pharmaceutical composition having inhibitory activity on 11β-hydroxysteroid dehydrogenase type 1 comprising a compound represented by the Formula (I):

[Formula 1]

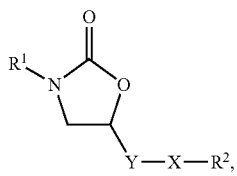

its pharmaceutically acceptable salt, or a solvate thereof,
wherein $R^1$ is optionally substituted arylalkyl, optionally substituted cycloalkyl, optionally substituted cycloalkylalkyl, optionally substituted heteroaryl, optionally substituted heteroarylalkyl, optionally substituted heterocycle or optionally substituted heterocyclealkyl,
X is —O—, —NR$^3$—, —NR$^3$C(=O)— or —NR$^3$S(=O)$_2$—,
$R^2$ is optionally substituted aryl, optionally substituted arylalkyl, optionally substituted cycloalkyl, optionally substituted cycloalkylalkyl, optionally substituted heteroaryl, optionally substituted heteroarylalkyl, optionally substituted heterocycle or optionally substituted heterocyclealkyl,
$R^3$ is hydrogen or optionally substituted alkyl,
Y is —(CR$^4$R$^5$)n-,
$R^4$ and $R^5$ are each independently hydrogen, optionally substituted alkyl, halogen or hydroxy, and
n is an integer of 1 to 6,
provided that, when $R^1$ is optionally substituted arylalkyl, and X is —O—, $R^2$ is not optionally substituted pyrano[2,3-d]pyrimidinyl or aryl substituted with thiazolidinedione-5-yl methyl, (2)
The pharmaceutical composition having inhibitory activity on 11β-hydroxysteroid dehydrogenase type 1 comprising the compound according to the above (1), its pharmaceutically acceptable salt, or a solvate thereof, wherein n is 1, and $R^4$ and $R^5$ are hydrogen, (3)
The pharmaceutical composition having inhibitory activity on 11β-hydroxysteroid dehydrogenase type 1 comprising the compound according to the above (2), its pharmaceutically acceptable salt, or a solvate thereof, wherein $R^1$ is optionally substituted cycloalkyl, optionally substituted cycloalkylalkyl, optionally substituted heteroaryl, optionally substituted heteroarylalkyl, optionally substituted heterocycle or optionally substituted heterocyclealkyl, (4)
A compound represented by the Formula (I):

[Formula 2]

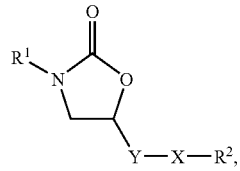

its pharmaceutically acceptable salt, or a solvate thereof,
wherein $R^1$ is optionally substituted arylalkyl, optionally substituted cycloalkyl, optionally substituted cycloalkylalkyl, optionally substituted heteroaryl, optionally substituted heteroarylalkyl, optionally substituted heterocycle or optionally substituted heterocyclealkyl,
X is —O—, —NR$^3$—, —NR$^3$C(=O)— or —NR$^3$S(=O)$_2$—,
$R^2$ is optionally substituted aryl, optionally substituted arylalkyl, optionally substituted cycloalkyl, optionally substituted cycloalkylalkyl, optionally substituted heteroaryl, optionally substituted heteroarylalkyl, optionally substituted heterocycle or optionally substituted heterocyclealkyl,
$R^3$ is hydrogen or optionally substituted alkyl,
Y is —(CR$^4$R$^5$)n-,
$R^4$ and $R^5$ are each independently hydrogen, optionally substituted alkyl, halogen or hydroxy, and
n is an integer of 1 to 6,
provided that, when $R^1$ is optionally substituted arylalkyl, $R^2$ is pyridyl substituted with trifluoromethyl group, optionally substituted cycloalkyl, optionally substituted cycloalkylalkyl; optionally substituted heteroarylalkyl, optionally substituted heterocycle or optionally substituted heterocyclealkyl, while when $R^1$ is unsubstituted cyclohexyl and X is —O—, $R^2$ is not optionally substituted phenyl or unsubstituted benzyl), (5)
The compound according to the above (4), its pharmaceutically acceptable salt, or a solvate thereof, wherein n is 1, and $R^4$ and $R^5$ are hydrogen, (6)
The compound according to the above (5), its pharmaceutically acceptable salt, or a solvate thereof, wherein $R^1$ is optionally substituted cycloalkyl having 7 or more carbon atoms, optionally substituted cycloalkylalkyl, optionally substituted heteroaryl, optionally substituted heteroarylalkyl, optionally substituted heterocycle or optionally substituted heterocyclealkyl, and $R^2$ is optionally substituted aryl, optionally substituted arylalkyl, optionally substituted cycloalkyl, optionally substituted cycloalkylalkyl, optionally substituted heteroaryl, optionally substituted heteroarylalkyl, optionally substituted heterocycle or optionally substituted heterocyclealkyl, (7)
The compound according to the above (5), its pharmaceutically acceptable salt, or a solvate thereof, wherein $R^1$ is optionally substituted arylalkyl or optionally substituted cycloalkyl, and $R^2$ is optionally substituted aryl, optionally substituted arylalkyl or optionally substituted heteroaryl, (8)
The compound according to any one of the above (5) to (7), its pharmaceutically acceptable salt, or a solvate thereof, wherein $R^1$ is optionally substituted cycloalkyl, (9)
The compound according to the above (8), its pharmaceutically acceptable salt, or a solvate thereof, wherein $R^1$ is optionally substituted cyclooctyl,
(10)
The compound according to any one of the above (5) to (9), its pharmaceutically acceptable salt, or a solvate thereof, wherein $R^2$ is optionally substituted aryl, optionally substituted arylalkyl or optionally substituted heteroaryl,
(11)
The compound according to any one of the above (5) to (10), its pharmaceutically acceptable salt, or a solvate thereof, wherein $R^3$ is optionally substituted alkyl,
(12)
A pharmaceutical composition comprising the compound according to any one of the above (4) to (11), its pharmaceutically acceptable salt, or a solvate thereof,
(13)
The pharmaceutical composition according to the above (12), which is an 11β-hydroxysteroid dehydrogenase type 1 inhibitor.
Further, the present invention includes:
(14)
The pharmaceutical composition according to any one of the above (1) to (3), (12) or (13), for treatment and/or prevention of diabetes,
(15)
A method for preventing or treating diabetes, comprising administering the compound according to any one of the above (1) to (11), its pharmaceutically acceptable salt, or a solvate thereof,
(16)
A use of the compound according to any one of the above (1) to (11), its pharmaceutically acceptable salt, or a solvate thereof for manufacturing a medicament of treatment and/or prevention of diabetes,
(17)
The compound according to any one of the above (1) to (11), its pharmaceutically acceptable salt, or a solvate thereof for treatment and/or prevention of diabetes.
Furthermore, as an intermediate of the present compound, the compound represented by the following formula is particularly useful.
(18)
A compound represented by the Formula (Ia):

[Formula 3]

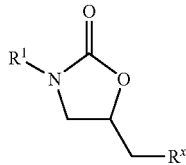

(Ia)

its pharmaceutically acceptable salt, or a solvate thereof,
wherein $R^1$ is optionally substituted arylalkyl, optionally substituted cycloalkyl, optionally substituted cycloalkylalkyl, optionally substituted heteroaryl, optionally substituted heteroarylalkyl, optionally substituted heterocycle or optionally substituted heterocyclealkyl,
$R^X$ is hydroxy, alkylsulfonyloxy or a group represented by the Formula: —NHR$^3$ (wherein $R^3$ is hydrogen or optionally substituted alkyl).

(19)
The compound according to the above (18), its pharmaceutically acceptable salt, or a solvate thereof, wherein $R^1$ is optionally substituted cycloalkyl having 7 or more carbon atoms, optionally substituted cycloalkylalkyl, optionally substituted heteroaryl, optionally substituted heteroarylalkyl, optionally substituted heterocycle or optionally substituted heterocyclealkyl.
(20)
A compound represented by the Formula:

[Formula 4]

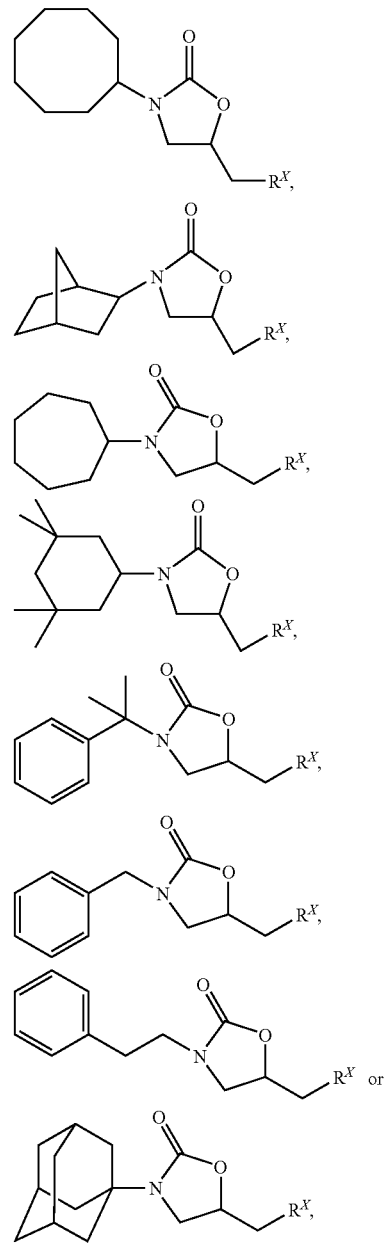

its pharmaceutically acceptable salt, or a solvate thereof,
wherein $R^X$ is hydroxy, alkylsulfonyloxy or a group represented by the Formula: —NHR$^3$ (wherein $R^3$ is hydrogen or optionally substituted alkyl).

(21)

The compound according to the above (19) or (20), its pharmaceutically acceptable salt, or a solvate thereof, wherein $R^x$ is hydroxy.

Effect of the Invention

Since the present compound has inhibitory activity on 11β-hydroxysteroid dehydrogenase type 1, pharmaceutical compositions comprising the present compound are very useful as medicaments, especially, as medicaments for treatment and/or prevention of hyperlipidemia, diabetes, obesity, arteriosclerosis, atherosclerosis, hyperglycemia, and/or syndrome X. Moreover, the present compound selectively inhibits 11β-hydroxysteroid dehydrogenase type 1, and is a compound having other utility as a medicament. Here, the utility as a medicament includes excellent metabolic stability, a weak drug-metabolizing enzyme induction, a weak inhibition of drug metabolizing enzyme that metabolizes other drug, a high oral absorption, a low clearance, a long half-life period enough to exhibit drug efficacy and so on.

BEST MODE FOR CARRYING OUT THE INVENTION

In the following, meanings of terms used in the present specification will be explained. Each term has the same meaning when used alone or in combination with other term in this description.

"Halogen" includes fluorine, chlorine, bromine or iodine. Particularly, fluorine, chlorine and bromine are preferable.

"Alkyl" means a C1 to C10 straight or branched alkyl group, and example includes methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl or the like. Preferable is C1 to C6 or C1 to C4 alkyl, and example includes methyl, ethyl, n-propyl, isopropyl, n-butyl, isobutyl, sec-butyl, tert-butyl, n-pentyl, isopentyl, neopentyl, n-hexyl or isohexyl.

"Cycloalkyl" means a C3 to C15 cyclic saturated hydrocarbon group, and example includes cyclopropyl, cyclobutyl, cyclopentyl, cyclohexyl, cycloheptyl, cyclooctyl, bridged cyclic hydrocarbon group, spiro hydrocarbon group or the like. Preferable is cyclopropyl, cyclobutyl, cyclopentyl, cyclohexyl or bridged cyclic hydrocarbon group.

"Bridged cyclic hydrocarbon group" includes a group which is derived by excluding one hydrogen from a C5 to C8 aliphatic cycle which consists of two or more rings that share two or more atoms. Example includes bicyclo[2.1.0]pentyl, bicyclo[2.2.1]heptyl, bicyclo[2.2.2]octyl, bicyclo[3.2.1]octyl, tricyclo[2.2.1.0]heptyl or the like.

"Spiro hydrocarbon group" includes a group which is derived by excluding one hydrogen from a cycle which consists of two hydrocarbon rings that share one carbon atom. Example includes spiro[3.4]octyl or the like.

"Aryl" means a monocyclic aromatic hydrocarbon group (e.g.: phenyl) and a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl). Preferable is phenyl or naphthyl (1-naphthyl or 2-naphthyl).

"Heteroaryl" means a monocyclic aromatic heterocyclic group or a fused aromatic heterocyclic group. The monocyclic aromatic heterocyclic group means a group derived from a 5- to 8-membered aromatic ring which may contain 1 to 4 oxygen, sulfur and/or nitrogen atom(s) in the ring, and may have a bond at a substitutable arbitrary position. The fused aromatic heterocyclic group means a group in which a 5- to 8-membered aromatic ring optionally containing 1 to 4 of an oxygen atom, a sulfur atom and/or a nitrogen atom in the ring is fused with 1 to 4 of 5- to 8-membered aromatic carbocycle(s) or other 5- to 8-membered aromatic heterocycle(s), and which may have a bond at a substitutable arbitrary position.

Example of the "heteroaryl" includes furyl (e.g.: 2-furyl or 3-furyl), thienyl (e.g.: 2-thienyl or 3-thienyl), pyrrolyl (e.g.: 1-pyrrolyl, 2-pyrrolyl or 3-pyrrolyl), imidazolyl (e.g.: 1-imidazolyl, 2-imidazolyl or 4-imidazolyl), pyrazolyl (e.g.: 1-pyrazolyl, 3-pyrazolyl or 4-pyrazolyl), triazolyl (e.g.: 1,2,4-triazole-1-yl, 1,2,4-triazole-3-yl or 1,2,4-triazole-4-yl), tetrazolyl (e.g.: 1-tetrazolyl, 2-tetrazolyl or 5-tetrazolyl), oxazolyl (e.g.: 2-oxazolyl, 4-oxazolyl or 5-oxazolyl), isoxazolyl (e.g.: 3-isoxazolyl, 4-isoxazolyl or 5-isoxazolyl), thiazolyl (e.g.: 2-thiazolyl, 4-thiazolyl or 5-thiazolyl), thiadiazolyl, isothiazolyl (e.g.: 3-isothiazolyl, 4-isothiazolyl or 5-isothiazolyl), pyridyl (e.g.: 2-pyridyl, 3-pyridyl or 4-pyridyl), pyridazinyl (e.g.: 3-pyridazinyl or 4-pyridazinyl), pyrimidinyl (e.g.: 2-pyrimidinyl, 4-pyrimidinyl or 5-pyrimidinyl), furazanyl (e.g.: 3-furazanyl), pyrazinyl (e.g.: 2-pyrazinyl), oxadiazolyl (e.g.: 1,3,4-oxadiazole-2-yl), benzofuryl (e.g.: 2-benzo[b]furyl, 3-benzo[b]furyl, 4-benzo[b]furyl, 5-benzo[b]furyl, 6-benzo[b]furyl or 7-benzo[b]furyl), benzothienyl (e.g.: 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g.: 1-benzimidazolyl, 2-benzimidazolyl, 4-benzimidazolyl or 5-benzimidazolyl), dibenzofuryl, benzoxazolyl, quinoxalinyl (e.g.: 2-quinoxalinyl, 5-quinoxalinyl or 6-quinoxalinyl), cinnolinyl (e.g.: 3-cinnolinyl, 4-cinnolinyl, 5-cinnolinyl, 6-cinnolinyl, 7-cinnolinyl or 8-cinnolinyl), quinazolinyl (e.g.: 2-quinazolinyl, 4-quinazolinyl, 5-quinazolinyl, 6-quinazolinyl, 7-quinazolinyl or 8-quinazolinyl), quinolyl (e.g.: 2-quinolyl, 3-quinolyl, 4-quinolyl, 5-quinolyl, 6-quinolyl, 7-quinolyl or 8-quinolyl), phthalazinyl (e.g.: 1-phthalazinyl, 5-phthalazinyl or 6-phthalazinyl), isoquinolyl (e.g.: 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g.: 2-pteridinyl, 4-pteridinyl, 6-pteridinyl or 7-pteridinyl), carbazolyl, phenanthridinyl, acridinyl (e.g.: 1-acridinyl, 2-acridinyl, 3-acridinyl, 4-acridinyl or 9-acridinyl), indolyl (e.g.: 1-indolyl, 2-indolyl, 3-indolyl, 4-indolyl, 5-indolyl, 6-indolyl or 7-indolyl), isoindolyl, phenadinyl (e.g.: 1-phenadinyl or 2-phenadinyl), phenothiadinyl (e.g.: 1-phenothiadinyl, 2-phenothiadinyl, 3-phenothiadinyl or 4-phenothiadinyl) or the like.

"Heterocycle" means a nonaromatic heterocyclic group which may contain 1 to 4 oxygen, sulfur and/or nitrogen atom(s) in the ring, and may have a bond at a substitutable arbitrary position. Moreover, the nonaromatic heterocyclic group can be bridged with a C1 to C4 alkyl chain, or can be fused with cycloalkane (5- to 6-membered ring is preferable) or benzene ring. Heterocycle can be saturated or unsaturated as long as it is non-aromatic. Preferable is a 5- to 8-membered ring. Example includes 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperadinyl, 2-piperadinyl, 2-morpholinyl, 3-morpholinyl, morpholino, tetrahydropyranyl or the like.

In "arylalkyl", "cycloalkylalkyl", "heteroarylalkyl" and "heterocyclealkyl", the alkyl part substituted with "aryl", "cycloalkyl", "heteroaryl" or "heterocycle" means the above "alkyl".

"Aryl", "cycloalkyl", "heteroaryl" and "heterocycle" parts in "arylalkyl", "cycloalkylalkyl", "heteroarylalkyl" and "heterocyclealkyl" mean the above "aryl", "cycloalkyl", "heteroaryl" and "heterocycle", respectively.

The alkyl part of "alkylsulfonyloxy" means the above "alkyl".

As a substituent on ring in "optionally substituted aryl", "optionally substituted arylalkyl", "optionally substituted cycloalkyl", "optionally substituted cycloalkylalkyl", "optionally substituted heteroaryl", "optionally substituted heteroarylalkyl", "optionally substituted heterocycle", and "optionally substituted heterocyclealkyl", it is selected from the group consisting of, for example, hydroxy, carboxy, halogen, halogenated alkyl (e.g.: $CF_3$, $CH_2CF_3$ or $CH_2CCl_3$), nitro, nitroso, cyano, alkyl (e.g.: methyl, ethyl, isopropyl or tert-butyl), alkenyl (e.g.: vinyl), alkynyl (e.g.: ethynyl), cycloalkyl (e.g.: cyclopropyl or adamantyl), cycloalkylalkyl (e.g.: cyclohexylmethyl or adamantylmethyl), cycloalkenyl (e.g.: cyclopropenyl), aryl (e.g.: phenyl or naphthyl), arylalkyl (e.g.: benzyl or phenethyl), heteroaryl (e.g.: pyridyl or furyl), heteroarylalkyl (e.g.: pyridylmethyl), heterocycle (e.g.: piperidyl), heterocyclealkyl (e.g.: morpholylmethyl), alkoxy (e.g.: methoxy, ethoxy, propoxy or butoxy), halogenated alkoxy (e.g.: $OCF_3$), alkenyloxy (e.g.: vinyloxy or allyloxy), alkoxycarbonyl (e.g.: methoxycarbonyl, ethoxycarbonyl or tert-butoxycarbonyl), arylalkyloxy (e.g.: benzyloxy), amino (e.g.: alkylamino (e.g.: methylamino, ethylamino or dimethylamino), acylamino (e.g.: acetylamino or benzoylamino), arylalkylamino (e.g.: benzylamino or tritylamino), hydroxyamino, alkylaminoalkyl (e.g.: diethylaminomethyl), sulfamoyl and the like. It may be substituted with 1 to 4 such substituent(s).

As a substituent for an alkyl part of "optionally substituted arylalkyl", "optionally substituted cycloalkylalkyl", "optionally substituted heteroarylalkyl", and "optionally substituted heterocyclealkyl", it is selected from the group consisting of, for example, hydroxy, alkyl (e.g.: methyl, ethyl, isopropyl or tert-butyl), alkoxy (e.g.: methoxy, ethoxy, propoxy or butoxy), halogen, halogenated alkyl (e.g.: $CF_3$, $CH_2CF_3$ or $CH_2CCl_3$), halogenated alkoxy (e.g.: $OCF_3$), cycloalkyl (e.g.: cyclopropyl or adamantyl), alkylene (e.g.: —$(CH_2)_2$—, —$(CH_2)_3$—, —$(CH_2)_4$— or —$(CH_2)_5$—) and the like. It may be substituted with 1 to 4 such substituent(s).

As a substituent for "optionally substituted alkyl", it is the same as the substituent for an alkyl part of the above "optionally substituted arylalkyl", "optionally substituted cycloalkylalkyl", "optionally substituted heteroarylalkyl", and "optionally substituted heterocyclealkyl".

"Alkenyl" means C2 to C8 straight or branched alkenyl having one or more double bond(s) in the above "alkyl", and example includes vinyl, 1-propenyl, 2-propenyl, 1-butenyl, 2-butenyl, 3-butenyl, 1,3-butadienyl, 3-methyl 2-butenyl or the like.

"Alkynyl" means C2 to C8 straight or branched alkynyl having one or more triple bond(s) in the above "alkyl", and example includes ethynyl, propinyl, butynyl or the like.

"Cycloalkenyl" means C3 to C7 cyclic unsaturated aliphatic hydrocarbon group, and example includes cyclopropenyl, cyclobutenyl, cyclopentenyl, cyclohexenyl, cycloheptenyl or the like. Preferable is cyclopropenyl, cyclobutenyl, cyclopentenyl or cyclohexenyl. Cycloalkenyl also includes bridged cyclic hydrocarbon group and spiro hydrocarbon group which have an unsaturated bond in the ring.

The alkyl part of "alkoxy" and "alkoxycarbonyl" means the above "alkyl".

The alkenyl part of "alkenyloxy" means the above "alkenyl".

The arylalkyl part of "arylalkyloxy" means the above "arylalkyl".

The halogen part, the alkyl part, and the alkoxy part of "halogenated alkyl" and "halogenated alkoxy" are the same as the above "halogen", "alkyl", and "alkoxy", respectively.

"Acylamino" means alkylcarbonylamino or arylcarbonylamino.

The alkyl part of "alkylcarbonylamino" is the same as the above "alkyl".

The aryl part of "arylcarbonylamino" is the same as the above "aryl".

As the "optionally substituted arylalkyl", particularly preferably, the following examples are included:

[Formula 5]

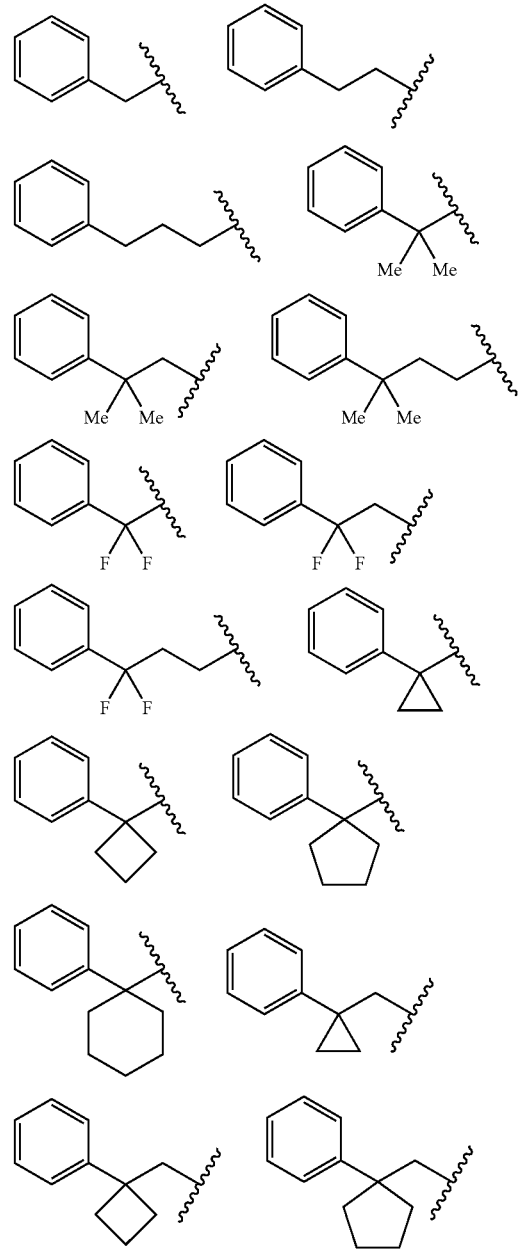

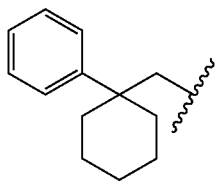

As the "optionally substituted cycloalkylalkyl", particularly preferably, the following examples are included:

[Formula 6]

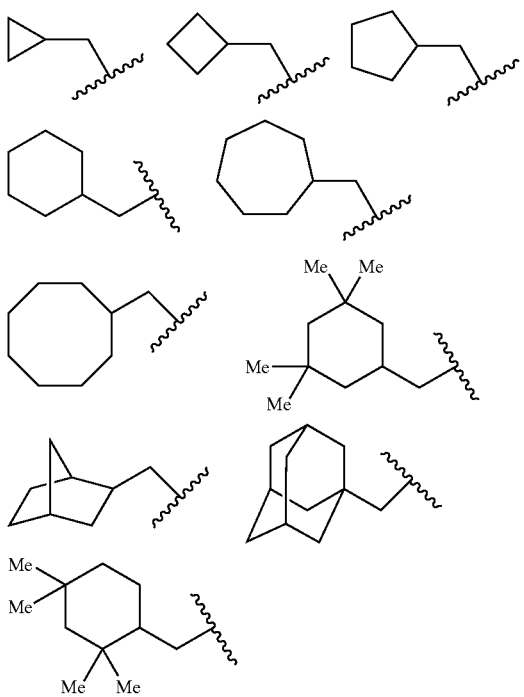

As the "heteroarylalkyl", particularly preferably, the following examples are included:

[Formula 7]

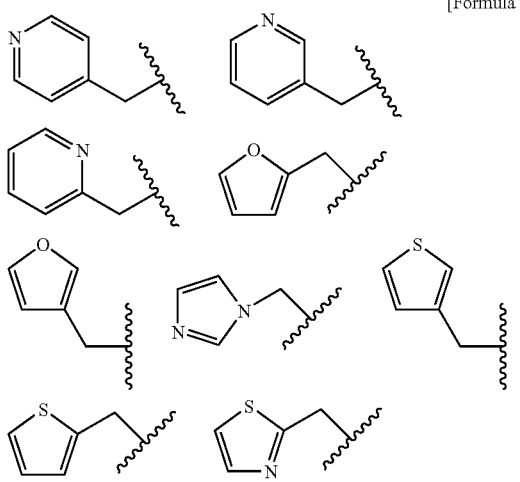

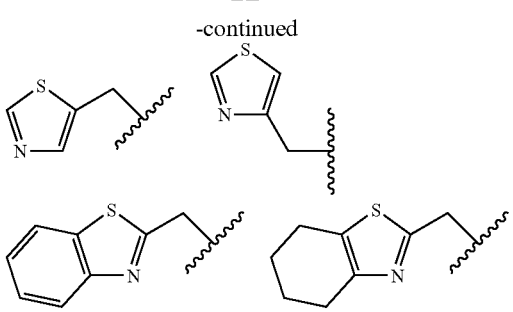

As the "optionally substituted heterocyclealkyl", particularly preferably, the following examples are included:

[Formula 8]

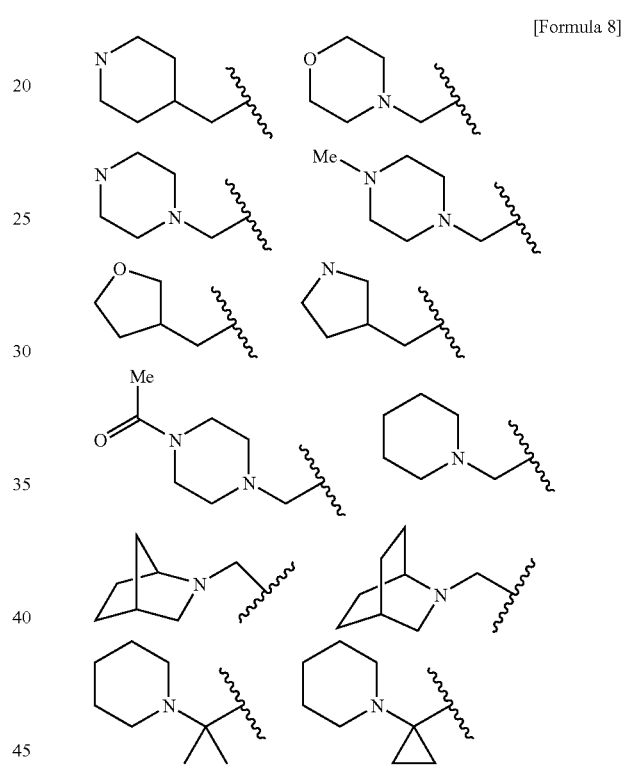

R¹ is optionally substituted arylalkyl, optionally substituted cycloalkyl, optionally substituted cycloalkylalkyl, optionally substituted heteroaryl, optionally substituted heteroarylalkyl, optionally substituted heterocycle or optionally substituted heterocyclealkyl. R¹ is preferably optionally substituted cycloalkyl or optionally substituted arylalkyl. More preferably R¹ is optionally substituted cyclooctyl.

In R¹, as a substituent on a ring of "optionally substituted arylalkyl", "optionally substituted cycloalkyl", "optionally substituted cycloalkylalkyl", "optionally substituted heteroaryl", "optionally substituted heteroarylalkyl", "optionally substituted heterocycle" or "optionally substituted heterocyclealkyl", preferable is alkyl, alkoxy, halogen, halogenated alkyl, halogenated alkoxy or hydroxy.

In R¹, as a substituent for an alkyl part of "optionally substituted arylalkyl", "optionally substituted cycloalkylalkyl", "optionally substituted heteroarylalkyl" or "optionally substituted heterocyclealkyl", preferable is alkyl, alkoxy, cycloalkyl, halogen, halogenated alkyl, halogenated alkoxy or hydroxy.

$R^2$ is optionally substituted aryl, optionally substituted arylalkyl, optionally substituted cycloalkyl, optionally substituted cycloalkylalkyl, optionally substituted heteroaryl, optionally substituted heteroarylalkyl, optionally substituted heterocycle or optionally substituted heterocyclealkyl. $R^2$ is preferably optionally substituted aryl, optionally substituted arylalkyl or optionally substituted heteroaryl.

In $R^2$, as a substituent on a ring of "optionally substituted aryl", "optionally substituted arylalkyl", "optionally substituted cycloalkyl", "optionally substituted cycloalkylalkyl", "optionally substituted heteroaryl", "optionally substituted heteroarylalkyl", "optionally substituted heterocycle" or "optionally substituted heterocyclealkyl", preferable is halogenated alkyl, halogenated alkoxy, halogen, alkyl, alkoxy, hydroxy, heterocyclealkyl, heteroarylalkyl or alkylaminoalkyl.

$R^3$ is hydrogen or optionally substituted alkyl. $R^3$ is preferably optionally substituted alkyl. $R^4$ and $R^5$ are each independently hydrogen, optionally substituted alkyl, halogen or hydroxy. $R^4$ and $R^5$ are preferably hydrogen.

n is an integer of 1 to 6. Especially, 1 is preferred.

X is —O—, —NR$^3$—, —NR$^3$C(=O)— or —NR$^3$S(=O)$_2$—, and preferable is —O— or —NR$^3$S(=O)$_2$—.

As a salt of the present compound, a pharmaceutically acceptable salt is preferable. As a pharmaceutically acceptable salt, the following salts can be included.

As a basic salt, example includes alkali metal salt such as sodium salt or potassium salt; alkaline earth metal salt such as calcium salt or magnesium salt; ammonium salt; aliphatic amine salt such as trimethylamine salt, triethylamine salt, dicyclohexylamine salt, ethanolamine salt, diethanolamine salt, triethanolamine salt, procaine salt, meglumine salt, diethanolamine salt or ethylenediamine salt; aralkylamine salt such as N,N-dibenzylethylenediamine salt or benethamine salt; heterocyclic aromatic amine salt such as pyridine salt, picoline salt, quinoline salt, or isoquinoline salt; quaternary ammonium salt such as tetramethylammonium salt, tetraethylammonium salt, benzyltrimethylammonium salt, benzyltriethylammonium salt, benzyltributylammonium salt, methyltrioctylammonium salt, or tetrabutylammonium salt; basic amino acid salt such as arginine salt or lysine salt or the like.

As an acidic salt, example includes inorganic acid salt such as hydrochloride, sulfate, nitrate, phosphate, carbonate, hydrogencarbonate, or perchlorate; organic acid salt such as acetate, propionate, lactate, maleate, fumarate, tartrate, malate, citrate or ascorbate; sulfonate such as methanesulfonate, isethionate, benzenesulfonate or p-toluenesulfonate; acidic amino acid salt such as aspartate or glutamate or the like.

The term "solvate" means a solvate of a compound of the present invention or a pharmaceutically acceptable salt thereof, and example includes alcohol (e.g.: ethanol) solvate, hydrate or the like. Example of hydrate includes monohydrate, dihydrate or the like.

A general method for producing the present compound is exemplified below. Also extraction, purification and the like may be conducted in a procedure executed in usual organic chemical experiment.

[Formula 9]

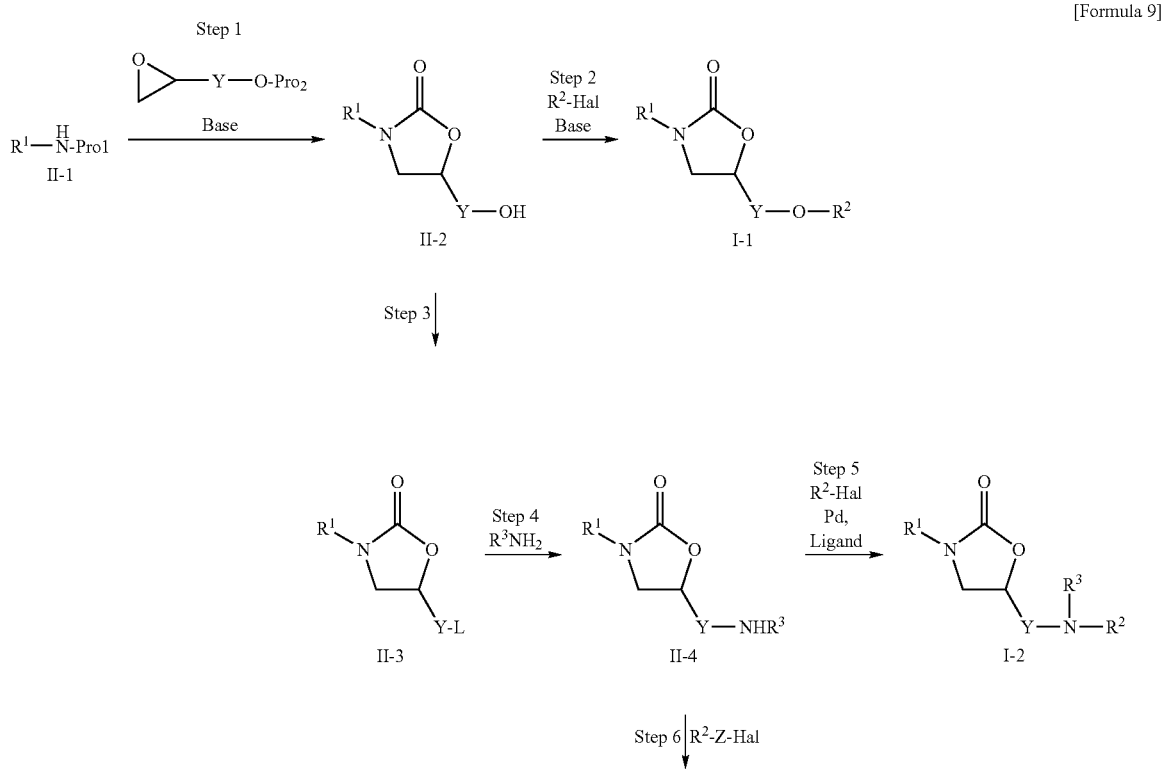

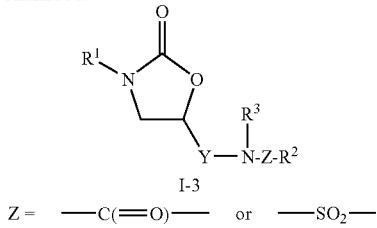

I-3

Z = —C(═O)— or —SO₂—

(wherein each symbol in the above scheme has the same meaning as the above, and as to compound (II-1), a known compound can be used, or a compound derived from a known compound by a usual method can be used. Pro1 is a protecting group of an amino group, Pro2 is a protecting group of a hydroxy group, Hal is halogen, and L is a leaving group. As a protecting group of an amino group, example includes an alkyloxycarbonyl group, an aryloxycarbonyl group or the like. As a protecting group of a hydroxy group, example includes a t-butyl group, a silyl group, an acyl group or the like. As a leaving group, example includes —OMs, —OTs, —OTf, —ONs or the like. Here, "Ms" represents methanesulfonyl group, "Ts" represents para-toluenesulfonyl group, "Tf" represents trifluoromethanesulfonyl group, and "Ns" represents ortho-nitrobenzenesulfonyl group.)

Step 1

Step 1 is a process for preparing an oxazolidinone derivative represented by the Formula (II-2) which comprises reacting the compound represented by the Formula (II-1) with epoxide.

As a solvent, example includes N-dimethylformamide, dimethylsulfoxide, aromatic hydrocarbons (e.g., toluene, benzene, xylene or the like), saturated hydrocarbons (e.g., cyclohexane, hexane or the like), halogenated hydrocarbons (e.g., dichloromethane, chloroform, 1,2-dichloroethane or the like), ethers (e.g., tetrahydrofuran, diethylether, dioxane, 1,2-dimethoxyethane or the like), esters (e.g., methyl acetate, ethyl acetate or the like), ketones (e.g., acetone, methylethylketone or the like), nitriles (e.g., acetonitrile or the like), alcohols (e.g., methanol, ethanol, t-butanol or the like), water, a mixed solvent thereof or the like.

As a base, example includes metal hydrides (e.g., sodium hydride or the like), metal hydroxides (e.g., sodium hydroxide, potassium hydroxide, lithium hydroxide, barium hydroxide or the like), metal carbonates (e.g., sodium carbonate, calcium carbonate, cesium carbonate or the like), metal alkoxides (e.g., sodium methoxide, sodium ethoxide, potassium t-butoxide or the like), sodium hydrogen carbonate, metal sodium, organic amines (e.g., triethylamine, diisopropylethylamine, DBU, 2,6-lutidine or the like), pyridine, alkyl lithiums (n-BuLi, sec-BuLi, tert-BuLi or the like) or the like.

Preferably, the reaction can be performed in a solvent of halogenated hydrocarbons (e.g., dichloromethane, chloroform or the like) or ethers (e.g., tetrahydrofuran, diethylether, dioxane or the like) with alkyl lithiums (n-BuLi, sec-BuLi or tert-BuLi) as a base. The reaction can be performed at −78 to 30° C. for 0.5 to 48 hours.

Step 2

Step 2 is a process for preparing the compound represented by the Formula (I-1) which comprises reacting the compound represented by the Formula (II-2) with the compound represented by the Formula (R²-Hal) in the presence of a base.

As a solvent, a solvent described in Step 1 can be used. Preferably, ethers (e.g., tetrahydrofuran, diethylether, dioxane, 1,2-dimethoxyethane or the like) or N-dimethylformamide can be used. As a base, a base described in Step 1 can be used. Preferably, metal hydrides (e.g., sodium hydride or the like) can be used.

The reaction can be performed at −20 to 30° C. for 0.5 to 24 hours.

Step 3

Step 3 is a process for preparing the compound represented by the Formula (II-3) which comprises converting a hydroxy group in the compound represented by the Formula (II-2) into a leaving group.

As a solvent, a solvent described in Step 1 can be used. Preferably, ethers (e.g., tetrahydrofuran, diethylether, dioxane, 1,2-dimethoxyethane or the like) can be used.

As a base, a base described in Step 1 can be used. Preferably, organic amines (e.g., triethylamine, diisopropylethylamine, DBU, 2,6-lutidine or the like) or pyridine can be used.

The reaction can be performed in the presence of mesyl chloride (MsCl), tosyl chloride (TsCl), trifluoromethanesulfonyl chloride (TfCl), trifluoromethanesulfonic anhydride (Tf₂O), nosyl chloride (NsCl) or the like, at −20 to 30° C. for 0.5 to 24 hours.

Step 4

Step 4 is a process for preparing the compound represented by the Formula (II-4) which comprises reacting the compound represented by the Formula (II-3) with the compound represented by the Formula (R³NH₂).

As a solvent, a solvent described in Step 1 can be used. Preferably, alcohols (e.g., methanol, ethanol, t-butanol or the like) can be used. The reaction can be performed at a temperature ranging from 30° C. to the temperature at which a solvent being used is refluxed, for 0.5 to 24 hours.

Step 5

Step 5 is a process for preparing the compound represented by the Formula (I-2) from the compound represented by the Formula (II-4) by palladium coupling.

As a solvent, a solvent described in Step 1 can be used. Preferably, aromatic hydrocarbons (e.g., toluene, benzene, xylene or the like) can be used.

As a base, a base described in Step 1 can be used. Preferably, metal carbonates (e.g., sodium carbonate, calcium carbonate, cesium carbonate or the like) or metal alkoxides (e.g., sodium methoxide, sodium ethoxide, potassium t-butoxide or the like) can be used. The reaction can be performed in the presence of palladium catalyst (e.g.: Pd(PPh₃)₄, PdCl₂, Pd(dba)₂ or the like) and phosphine ligand (e.g.: PPh₃, BINAP or the like) at a temperature ranging from 50° C. to the temperature at which a solvent being used is refluxed, for 0.5 to 24 hours.

Step 6

Step 6 is a process for preparing the compound represented by the Formula (I-3) which comprises reacting the compound represented by the Formula (II-4) with the compound represented by the Formula (R²—Z-Hal).

As a solvent, a solvent described in Step 1 can be used. Preferably, ethers (e.g., tetrahydrofuran, diethylether, dioxane, 1,2-dimethoxyethane or the like) can be used.

As a base, a base described in Step 1 can be used. Preferably, organic amines (e.g., triethylamine, diisopropylethylamine, DBU, 2,6-lutidine or the like) can be used. The reaction can be performed at −20 to 30° C. for 0.5 to 6 hours.

Various substituents in the present compound can be introduced by referring to (1) Alan R. Katriszly et al., Comprehensive Heterocyclic Chemistry (2) Alan R. Katriszly et al., Comprehensive Heterocyclic Chemistry II (3) RODD'S CHEMISTRY OF CARBON COMPOUNDS VOLUME IV HETEROCYCLIC COMPOUNDS or the like.

The present compound has excellent inhibitory activity on 11β-hydroxysteroid dehydrogenase type 1. Therefore, it can be used for treatment or prevention of a disease concerning 11β-hydroxysteroid dehydrogenase type 1, especially, disease such as hyperlipidemia, diabetes, obesity, arteriosclerosis, atherosclerosis, hyperglycemia and/or syndrome X. It is particularly useful in treatment or prevention of diabetes.

The compound used in the present invention can be administered orally or parenterally. In the case of oral administration, the compound used in the present invention can be used in any dose form including normal formulations, for example, solid formulations such as a tablet, powder, granule, capsule or the like; aqueous formulations; oleaginous suspensions; or liquid formulations such as syrup or elixir. In the case of parenteral administration, the compound used in the present invention can be used as an aqueous or oleaginous suspension for injection or nasal solution. In preparation of such formulations, a conventional excipient, binder, lubricant, aqueous solvent, oleaginous solvent, emulsifying agent, suspending agent, preservative, stabilizer and the like can be optionally used. Especially, using in a form of an oral formulation is preferred.

A formulation of the compound used in the present invention can be produced by combining (e.g., mixing) a therapeutically effective amount of the compound used in the present invention with a pharmaceutically acceptable carrier or diluent. Formulation of the compound used in the present invention can be produced by a known method using a well-known easily available ingredient.

A dosage of the compound used in the present invention differs depending on the administration route, age, body weight, condition and kind of disease of the patient, and is typically, about 0.05 mg to 3000 mg and preferably about 0.1 mg to 1000 mg per a day for adult person, in the case of oral administration, and can be administered in divided doses as necessary. In the case of parenteral administration, about 0.01 mg to 1000 mg and preferably about 0.05 mg to 500 mg per a day for adult person can be administered. In administration, it can be used together with other therapeutic agents.

In the following, the present invention will be described in more detail by way of examples which are not intended to limit the scope of the present invention.

Reference Example 1

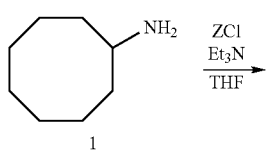

[Formula 10]

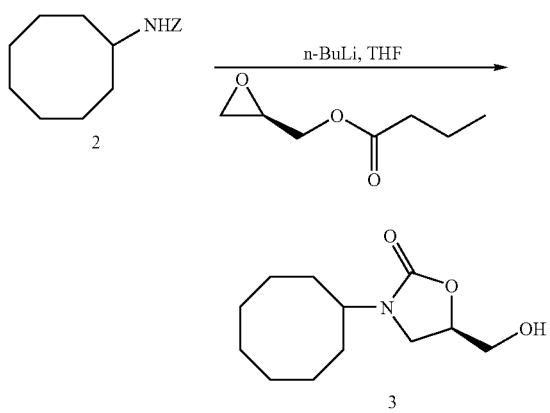

To a mixture of 3.7 mL (0.02594 mol) of benzyloxycarbonyl chloride (ZCl) and 15 mL of tetrahydrofuran were added 3 g (0.02358 mol) of cyclooctylamine (Compound 1) and 3.6 mL (0.02594 mol) of triethylamine under ice cooling, and the reaction solution was stirred for 24 hours at room temperature. After extraction by adding water and ethyl acetate to the reaction solution, the organic layer was washed with saturated saline, and dried with sodium sulfate. After removing the solvent under reduced pressure, the residue was purified by silica gel column chromatography (n-hexane:ethyl acetate=5:1), to obtain 4.54 g (74%) (Compound 2) of a colorless liquid.

To a mixture of 5.25 g (0.02009 mole) of Compound 2 and 52 mL of anhydrous tetrahydrofuran was added 13.3 mL (0.02109 mol) of n-butyl lithium (1.58 mol/L) dropwisely under argon atmosphere at −78° C., and the resulting mixture was stirred for 1 hour. To the resulting solution was added 2.98 mL (0.02109 mol) of (R) glycidyl butylate, and the reaction solution was stirred for 14 hours at room temperature. After extraction by adding water and ethyl acetate to the reaction solution, the organic layer was washed with saturated saline and dried with sodium sulfate. After removing the solvent under reduced pressure, the residue was purified by silica gel column chromatography (n-hexane:ethyl acetate=1:3), to obtain 2.21 g (14%) (Compound 3) of a colorless liquid.

1H-NMR (CDCl3): δ(ppm) 1.43-1.82 (14H, m), 2.07 (1H, t, J=6.5 Hz), 3.42 (1H, dd, J=8.5, 6.5 Hz), 3.56 (1H, t, J=8.5 Hz), 3.60-3.70 (1H, m), 3.82-3.98 (2H, m), 4.52-4.62 (1H, m).

The compounds shown below were synthesized in a similar manner.

Reference Example 2

[Formula 11]

(Compound 3-1) yield 12%, 1H-NMR (CDCl3): δ(ppm) 1.40-1.80 (14H, m), 2.05-2.21 (1H, m), 3.43 (1H, t, J=6.5 Hz), 3.56 (1H, t, J=9 Hz), 3.60-3.70 (1H, m), 3.8-4.00 (2H, m), 4.52-4.63 (1H, m).

Reference Example 3

[Formula 12]

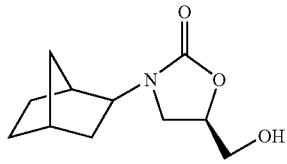

(Compound 3-2) yield 14%, 1H-NMR (CDCl3): δ(ppm) 1.10-1.83 (8H, m), 2.25-2.36 (2H, m), 2.43 (1H, brs), 3.40-3.73 (3H, m), 3.73-3.94 (2H, m), 4.50-4.62 (1H, m).

Reference Example 4

[Formula 13]

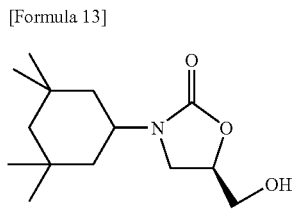

(Compound 3-3) yield 16%, 1H-NMR (CDCl3): δ(ppm) 0.85-1.30 (16H, m), 1.45-1.75 (3H, m), 3.39 (1H, dd, J=8.5, 6.5 Hz), 3.52 (1H, t, J=8.5 Hz), 3.64 (1H, dd, J=12.5, 4.5 Hz), 3.86 (1H, dd, J=12.5, 3.5 Hz), 4.02 (1H, dd, J=12.5, 3.5 Hz), 4.53-4.63 (1H, m).

Reference Example 5

[Formula 14]

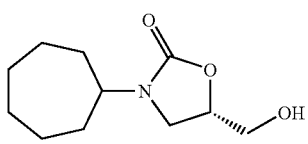

(Compound 3-4) yield 4%, 1H-NMR (CDCl3): δ(ppm) 1.40-2.05 (13H, m), 3.43 (1H, dd, J=8.5, 6.5 Hz), 3.55 (1H, t, J=8.5 Hz), 3.63 (1H, dd, J=12.5, 4.5 Hz), 3.80-3.95 (2H, m), 4.53-4.63 (1H, m).

Reference Example 6

[Formula 15]

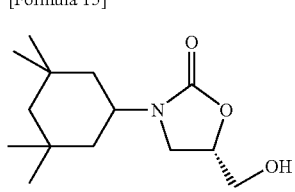

(Compound 3-5) yield 15%, 1H-NMR (CDCl3): δ(ppm) 0.93 (6H, s), 0.95-1.05 (1H, m), 1.08 (6H, s), 1.10-1.30 (3H, m), 1.48-1.60 (2H, m), 2.20 (1H, brs), 3.39 (1H, dd, J=8.5, 6.5 Hz), 3.52 (1H, t, J=8.5 Hz), 3.60-3.73 (1H, m), 3.85 (1H, dd, J=12.5, 3.5 Hz), 4.02 (1H, dd, J=12.5, 3.5 Hz), 4.53-4.64 (1H, m).

Reference Example 7

[Formula 16]

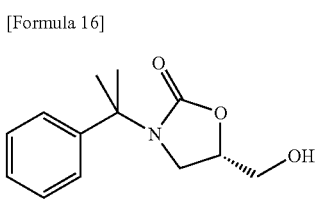

(Compound 3-6) yield 3%, 1H-NMR (DMSO): δ(ppm) 1.60 (3H, s), 1.83 (3H, s), 3.42-3.54 (2H, m), 3.54-3.63 (1H, m), 3.69 (1H, t, J=9 Hz), 4.41-4.51 (1H, m), 5.15 (1H, t, J=6 Hz), 7.17-7.25 (1H, m), 7.26-7.42 (4H, m).

Reference Example 8

[Formula 17]

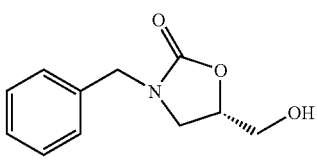

(Compound 3-7) yield 35%, 1H-NMR (CDCl3): δ(ppm) 2.53 (1H, brs), 3.33 (1H, dd, J=8.5, 7 Hz), 3.44 (1H, t, J=8.5 Hz), 3.61 (1H, br-d, J=12.5 Hz), 3.85 (1H, br-d, J=12 Hz), 4.37 (1H, d, J=15 Hz), 4.49 (1H, d, J=15 Hz), 4.54-4.63 (1H, m), 7.24-7.41 (5H, m).

Reference Example 9

[Formula 18]

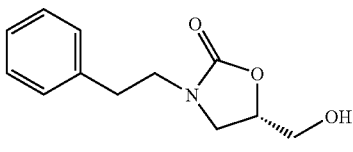

(Compound 3-8) yield 14%, 1H-NMR (CDCl3): δ(ppm) 2.10 (1H, brs), 2.89 (2H, t, J=7.5 Hz), 3.30 (1H, dd, J=8.5, 7 Hz), 3.42 (1H, t, J=8.5 Hz), 3.48-3.65 (3H, m), 3.72-3.85 (1H, m), 4.46-4.58 (1H, m), 7.20-7.38 (5H, m).

Example 1

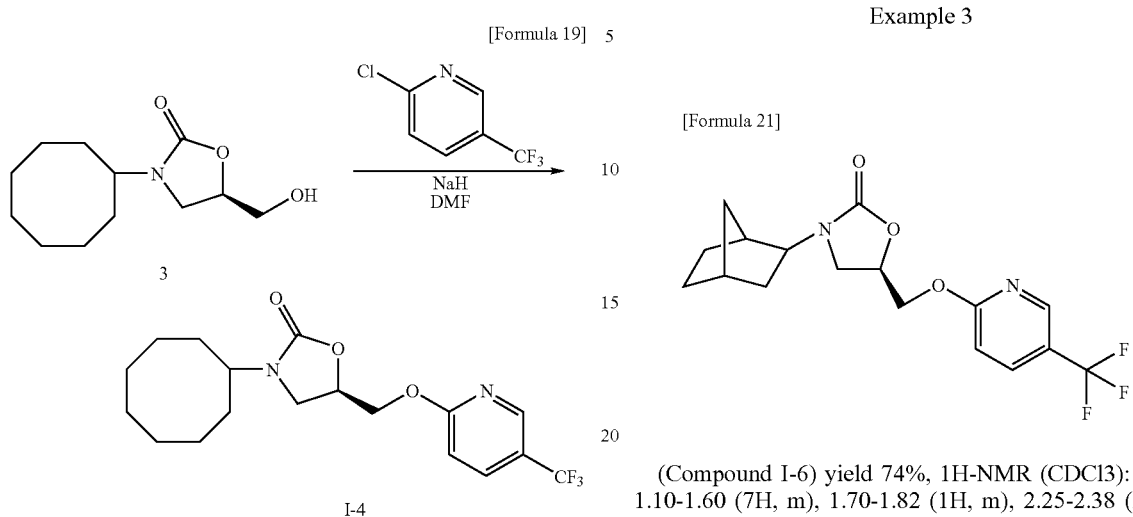

[Formula 19]

To a suspension of 83 mg (2.068 mmol) of sodium hydride in 5 mL of anhydrous dimethylformamide were added a mixture of 0.47 g (2.068 mmol) of Compound 3 and 5 mL of anhydrous dimethylformamide, and the resulting mixture was stirred for 1 hour at room temperature. To the resulting solution was added 0.38 g (2.068 mmol) of 2-chloro-5-trifluoromethylpyridine, and the reaction solution was stirred for 14 hours. After extraction by adding water and ethyl acetate to the reaction solution, the organic layer was washed with saturated saline and dried with sodium sulfate. After removing the solvent under reduced pressure, the residue was purified by silica gel column chromatography (n-hexane:ethyl acetate=4:1), to obtain 90 mg (12%) (Compound I-4) of colorless solid.

(Compound I-4) 1H-NMR (CDCl3): δ(ppm) 1.48-1.80 (14H, m), 3.44 (1H, dd, J=8.5, 6.5 Hz), 3.69 (1H, t, J=8.5 Hz), 3.93-4.04 (1H, m), 4.52 (2H, d, J=5 Hz), 4.80-4.90 (1H, m), 6.86 (1H, d, J=8.5, 2.5 Hz), 7.80 (1H, dd, J=8.5, 2.5 Hz), 8.42 (1H, d, J=2.5 Hz).

The compounds shown below were synthesized in a similar manner.

Example 2

[Formula 20]

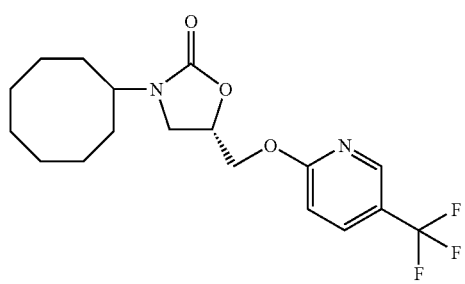

(Compound I-5) yield 61%, 1H-NMR (CDCl3): δ(ppm) 1.45-1.85 (14H, m), 3.44 (1H, dd, J=8.5, 6.5 Hz), 3.69 (1H, t, J=8.5 Hz), 3.92-4.04 (1H, m), 4.52 (2H, d, J=4.5 Hz), 4.79-4.90 (1H, m), 6.86 (1H, d, J=8.5 Hz), 7.80 (1H, dd, J=8.5, 2.5 Hz), 8.42 (1H, d, J=2.5 Hz).

Example 3

[Formula 21]

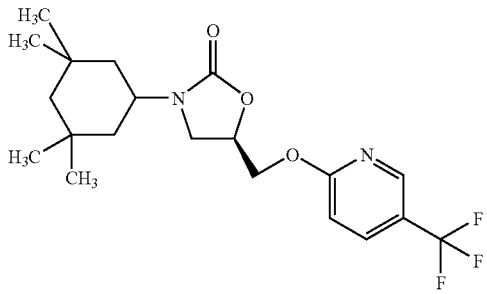

(Compound I-6) yield 74%, 1H-NMR (CDCl3): δ(ppm) 1.10-1.60 (7H, m), 1.70-1.82 (1H, m), 2.25-2.38 (2H, m), 3.42-3.54 (1H, m), 3.66-3.75 (1H, m), 3.80-3.87 (1H, m), 4.50-4.58 (2H, m), 4.78-4.90 (1H, m), 6.87 (1H, d, J=8.5 Hz), 7.81 (1H, d, J=8.5 Hz), 8.42 (1H, s).

Example 4

[Formula 22]

(Compound I-7) yield 80%, 1H-NMR (CDCl3): δ(ppm) 0.90-1.32 (16H, m), 1.46-1.60 (2H, m), 3.40 (1H, dd, J=9, 6 Hz), 3.65 (1H, t, J=9 Hz), 4.00-4.15 (1H, m), 4.53 (2H, dd, J=5, 1 Hz), 4.80-4.92 (1H, m), 6.87 (1H, d, J=8.5 Hz), 7.80 (1H, dd, J=8.5, 2.5 Hz), 8.42 (1H, d, J=2.5 Hz).

Example 5

[Formula 23]

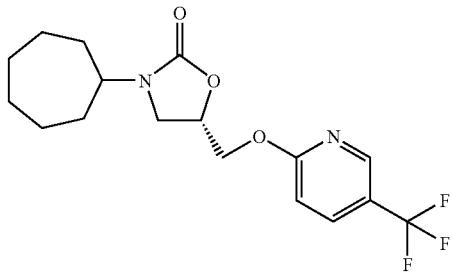

(Compound I-8) yield 43%, 1H-NMR (CDCl3): δ(ppm) 1.40-1.95 (12H, m), 3.44 (1H, dd, J=9, 6 Hz), 3.68 (1H, t, J=9 Hz), 3.84-3.96 (1H, m), 4.52 (2H, d, J=4.5 Hz), 4.80-4.90 (1H, m), 6.86 (1H, d, J=8.5 Hz), 7.80 (1H, dd, J=8.5, 2.5 Hz), 8.42 (1H, d, J=2.5 Hz).

Example 6

[Formula 24]

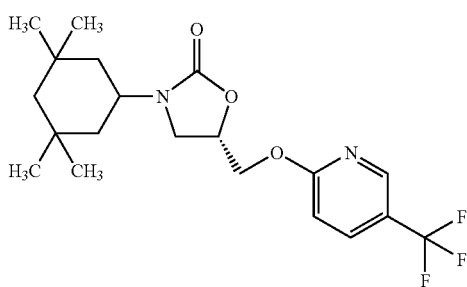

(Compound I-9) yield 85%, 1H-NMR (CDCl3): δ(ppm) 0.93 (6H, s), 1.09 (6H, s), 1.10-1.35 (4H, m), 1.45-1.60 (2H, m), 3.40 (1H, dd, J=9, 6 Hz), 3.65 (1H, t, J=9 Hz), 4.00-4.15 (1H, m), 4.53 (2H, dd, J=5, 2 Hz), 4.82-4.90 (1H, m), 6.87 (1H, d, J=9 Hz), 7.80 (1H, dd, J=9, 2 Hz), 8.43 (1H, d, J=2 Hz).

Example 7

[Formula 25]

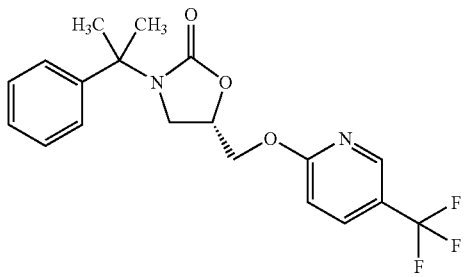

(Compound I-10) yield 26%, 1H-NMR (CDCl3): δ(ppm) 1.79 (3H, s), 1.80 (3H, s), 3.38 (1H, dd, J=9, 6 Hz), 3.62 (1H, t, J=9 Hz), 4.48 (1H, dd, J=12, 5 Hz), 4.53 (1H, dd, J=12, 4 Hz), 4.73-4.84 (1H, m), 6.87 (1H, d, J=8.5 Hz), 7.21-7.48 (5H, m), 7.81 (1H, dd, J=8.5, 2.5 Hz), 8.41 (1H, d, J=2.5 Hz).

Example 8

[Formula 26]

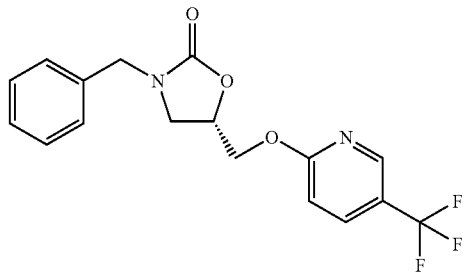

(Compound I-11) yield 65%, 1H-NMR (CDCl3): δ(ppm) 3.34 (1H, dd, J=9, 6 Hz), 3.57 (1H, t, J=9 Hz), 4.38-4.60 (4H, m), 4.82-4.94 (1H, m), 6.80 (1H, d, J=9 Hz), 7.24-7.44 (5H, m), 7.78 (1H, dd, J=9, 2.5 Hz), 8.38 (1H, d, J=2.5 Hz).

Example 9

[Formula 27]

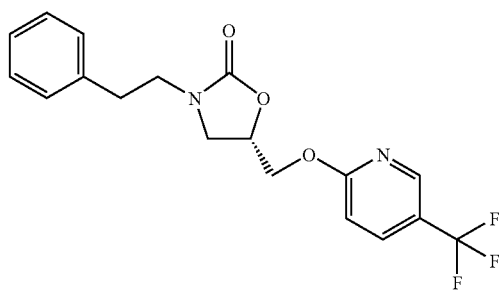

(Compound I-12) yield 45%, 1H-NMR (CDCl3): δ(ppm) 2.91 (2H, t, J=7 Hz), 3.30 (1H, dd, J=8.5, 6 Hz), 3.50-3.65 (3H, m), 4.44 (2H, d, J=5 Hz), 4.74-4.86 (1H, m), 6.82 (1H, d, J=8.5 Hz), 7.19-7.35 (5H, m), 7.79 (1H, d, J=8.5, 2 Hz), 8.41 (1H, d, J=2.5 Hz).

Reference Example 10

[Formula 28]

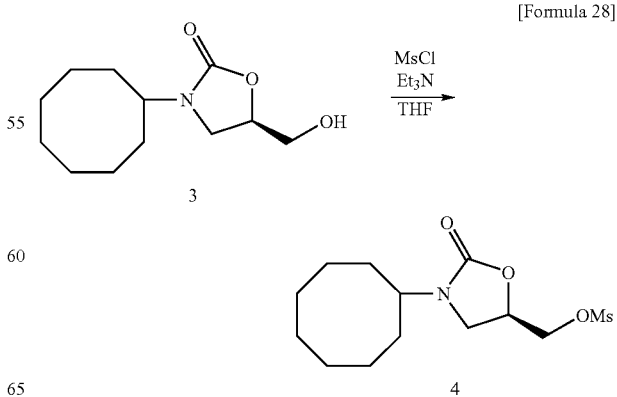

To a mixture of 10.62 g (2.728 mmol) of Compound 3, 0.42 mL (3.001 mmol) of triethylamine and 3.1 mL of anhydrous tetrahydrofuran was added 0.23 mL (3.001 mmol) of methanesulfonyl chloride dropwisely under ice cooling, and the reaction solution was stirred for 15.5 hours at room temperature. After extraction by adding water and ethyl acetate to the reaction solution, the organic layer was washed with saturated saline and dried with sodium sulfate. After removing the solvent under reduced pressure, the residue was purified by silica gel column chromatography (n-hexane:ethyl acetate=1:1), to obtain 0.80 g (96%) (Compound 4) of a colorless liquid.

H-NMR (CDCl3): δ(ppm) 1.45-1.80 (14H, m), 3.09 (3H, s), 3.42 (1H, dd, J=9, 6 Hz), 3.67 (1H, t, J=9 Hz), 3.88-4.00 (1H, m), 4.30 (1H, dd, J=11.5, 4.5 Hz), 4.38 (1H, dd, J=11.5, 4.5 Hz), 4.68-4.78 (1H, m).

Compounds shown below were synthesized in a similar manner.

Reference Example 11

[Formula 29]

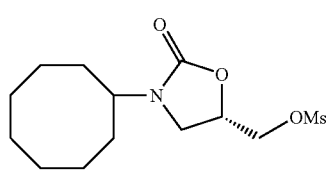

(Compound 4-1) yield 100%, 1H-NMR (CDCl3): δ(ppm) 1.45-1.80 (14H, m), 3.09 (3H, s), 3.43 (1H, dd, J=9, 5.5 Hz), 3.68 (1H, t, J=9 Hz), 3.86-4.00 (1H, m), 4.30 (1H, dd, J=11.5, 4.5 Hz), 4.38 (1H, dd, J=11.5, 4.5 Hz), 4.66-4.78 (1H, m).

Reference Example 12

[Formula 30]

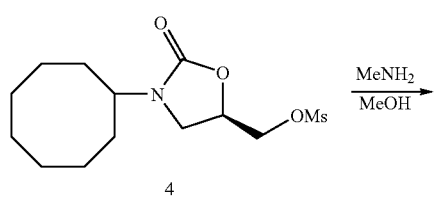

To a mixture of 0.40 g (1.310 mmole) of Compound 4 and 4 mL of methanol was added 3.3 mL of methylamine aqueous solution (12 mol/L), and the resulting mixture was refluxed for 8 hours under heating. After removing the solvent from the reaction solution under reduced pressure, the residue was extracted by adding water and ethyl acetate, and then the organic layer was washed with saturated saline and dried with sodium sulfate. The solvent was removed under reduced pressure to obtain 0.26 g (83%)(Compound 5) of a pale yellow liquid.

1H-NMR (CDCl3): δ(ppm) 1.40-1.80 (15H, m), 2.46 (3H, s), 2.79 (2H, d, J=6.5 Hz), 3.28 (1H, dd, J=8.5, 6.5 Hz), 3.57 (1H, t, J=8.5 Hz), 3.88-4.00 (1H, m), 4.54-4.64 (1H, m).

The compounds shown below were synthesized in a similar manner.

Reference Example 13

[Formula 31]

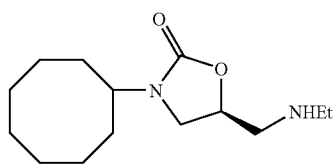

(Compound 5-1) yield 78%, 1H-NMR (CDCl3): δ(ppm) 1.11 (3H, t, J=7 Hz), 1.40-1.80 (15H, m), 2.68 (2H, qd, J=7, 2 Hz), 2.82 (2H, d, J=6 Hz), 3.28 (1H, dd, J=8.5, 6.5 Hz), 3.58 (1H, t, J=8.5 Hz), 3.88-4.00 (1H, m), 4.54-4.66 (1H, m).

Reference Example 14

[Formula 32]

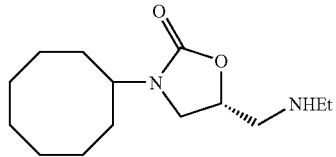

(Compound 5-2) yield 82%, 1H-NMR (CDCl3): δ(ppm) 1.11 (3H, t, J=7 Hz), 1.40-1.83 (15H, m), 2.68 (2H, qd, J=7, 2 Hz), 2.82 (2H, d, J=5.5 Hz), 3.28 (1H, dd, J=8.5, 6.5 Hz), 3.58 (1H, t, J=8.5 Hz), 3.87-4.00 (1H, m), 4.54-4.65 (1H, m).

Reference Example 15

[Formula 33]

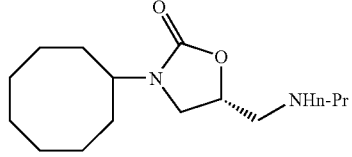

(Compound 5-3) yield 93%, 1H-NMR (CDCl3): δ(ppm) 0.91 (3H, t, J=7.5 Hz), 1.40-1.80 (17H, m), 2.50-2.65 (2H, m), 2.81 (2H, d, J=6 Hz), 3.28 (1H, dd, J=8.5, 6.5 Hz), 3.57 (1H, t, J=8.5 Hz), 3.87-3.98 (1H, m), 4.54-4.64 (1H, m).

Reference Example 16

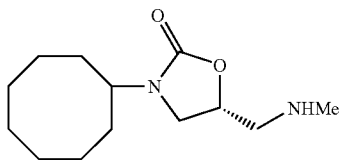

(Compound 5-4) yield 89%, 1H-NMR (CDCl3): δ(ppm) 1.42-1.85 (15H, m), 2.47 (3H, s), 2.79 (2H, d, J=6.5 Hz), 3.28 (1H, dd, J=8.5, 6.5 Hz), 3.57 (1H, t, J=8.5 Hz), 3.88-4.00 (1H, m), 4.54-4.65 (1H, m).

Reference Example 17

[Formula 35]

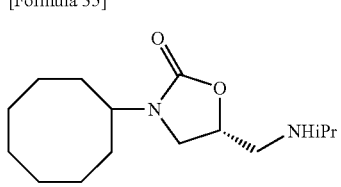

(Compound 5-5) yield 76%, 1H-NMR (DMSO): δ(ppm) 0.96 (6H, d, J=6.5 Hz), 1.40-1.75 (14H, m), 2.66 (2H, d, J=6 Hz), 2.67-2.77 (1H, m), 3.24 (1H, dd, J=8.5, 6.5 Hz), 3.53 (1H, t, J=8.5 Hz), 3.64-3.76 (1H, m), 4.39-4.49 (1H, m).

Example 10

[Formula 36]

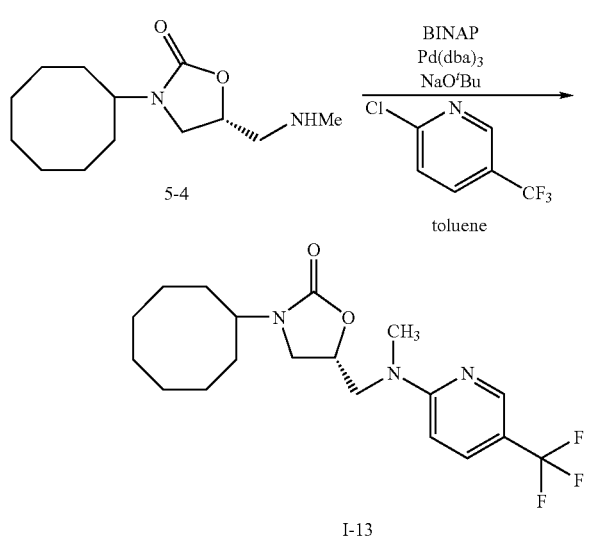

To a mixture of 1.2 mg of tris(dibenzylidene acetone)dipalladium, 3 mg of 2,2-bis(diphenylphosphino)-1,1-binaphthyl, 73 mg of sodium tert-butoxide and 5 mL of toluene were added 130 mg (0.5409 mmol) of Compound 5-4 and 98 mg of 2-chloro-5-trifluoromethylpyridine successively, and the resulting mixture was stirred for 6 hours at 100° C. under argon atmosphere. After extraction by adding water and ethyl acetate to the reaction solution, the organic layer was washed with saturated saline and dried with sodium sulfate. After removing the solvent under reduced pressure, the residue was purified by silica gel column chromatography (n-hexane: ethyl acetate=1:1), to obtain 29 mg (14%) (I-13) of a yellow liquid.

1H-NMR (CDCl3): δ(ppm) 1.43-1.75 (14H, m), 3.16 (3H, s), 3.31 (1H, dd, J=9, 6.5 Hz), 3.59 (1H, t, J=9 Hz), 3.77 (1H, dd, J=15, 6.5 Hz), 3.85-3.97 (1H, m), 4.12 (1H, dd, J=15, 3 Hz), 4.70-4.83 (1H, m), 6.54 (1H, d, J=9 Hz), 7.65 (1H, dd, J=9, 2.5 Hz), 8.34 (1H, d, J=2.5 Hz).

The compounds shown below were synthesized in a similar manner.

Example 11

[Formula 37]

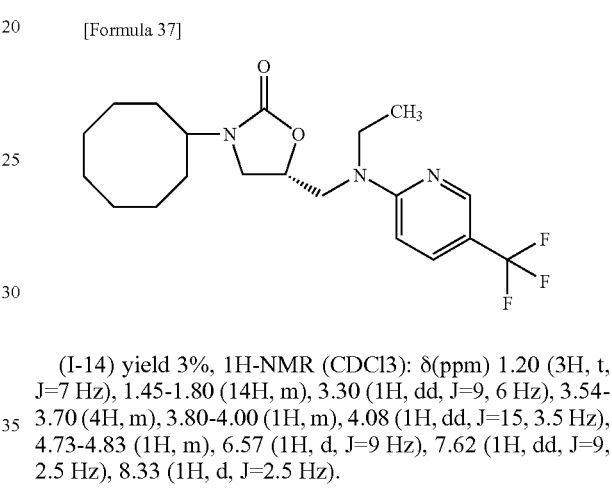

(I-14) yield 3%, 1H-NMR (CDCl3): δ(ppm) 1.20 (3H, t, J=7 Hz), 1.45-1.80 (14H, m), 3.30 (1H, dd, J=9, 6 Hz), 3.54-3.70 (4H, m), 3.80-4.00 (1H, m), 4.08 (1H, dd, J=15, 3.5 Hz), 4.73-4.83 (1H, m), 6.57 (1H, d, J=9 Hz), 7.62 (1H, dd, J=9, 2.5 Hz), 8.33 (1H, d, J=2.5 Hz).

Example 12

[Formula 38]

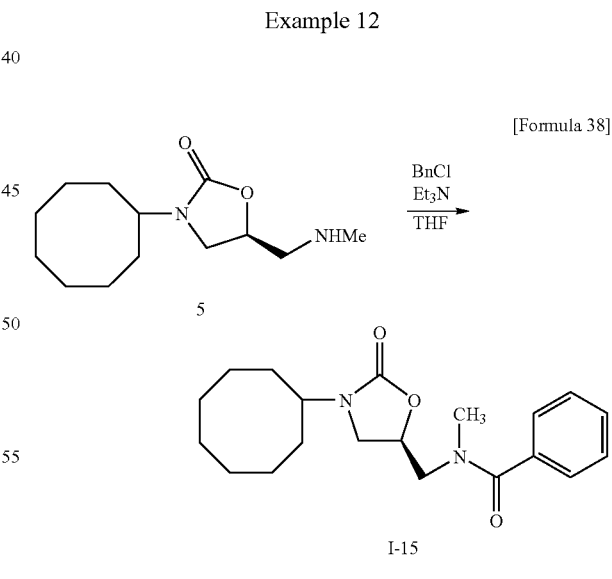

To a mixture of 30 mg (0.1248 mmole) of Compound 5, 14 mg (0.1373 mmol) of triethylamine and 1 mL of tetrahydrofuran was added a mixture of 19 mg of benzoyl chloride in 1 mL of tetrahydrofuran, and the reaction solution was stirred for 1 hour at room temperature. After extraction by adding water and ethyl acetate to the reaction solution, the organic layer was washed with saturated saline and dried with sodium sulfate. After removing the solvent under reduced pressure, the residue was purified by silica gel column chromatography (n-hexane:ethyl acetate=1:1), to obtain 0.80 g (84%) (I-15) of a colorless liquid.

1H-NMR (CDCl3): δ(ppm) 1.40-1.80 (14H, m), 3.13 (3H, s), 3.37 (1H, t, J=7.5 Hz), 3.54 (1H, dd, J=14.5, 7 Hz), 3.66 (1H, t, J=9 Hz), 3.90-4.10 (2H, m), 4.75-4.90 (1H, m), 7.34-7.46 (5H, m).

The compounds shown below were synthesized in a similar manner.

Example 13

[Formula 39]

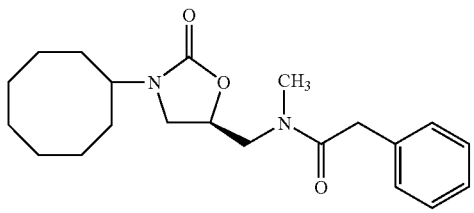

(Compound I-16) yield 74%, 1H-NMR (CDCl3): δ(ppm) 1.45-1.75 (14H, m), 3.15 (3H, s), 3.22 (1H, dd, J=9, 7 Hz), 3.41 (1H, dd, J=14.5, 6.5 Hz), 3.54 (1H, t, J=9 Hz), 3.73 (2H, s), 3.85 (1H, d, J=14.5, 3 Hz), 3.86-3.95 (1H, m), 4.64-4.70 (1H, m), 7.20-7.38 (5H, m).

Example 14

[Formula 40]

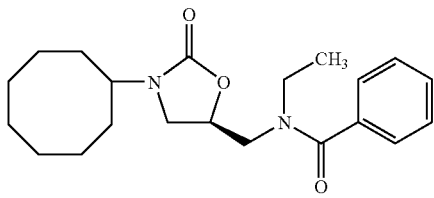

(Compound I-17) yield 79%, 1H-NMR (CDCl3): δ(ppm) 1.10 (3H, t, J=6.5 Hz), 1.47-1.80 (14H, m), 3.30-3.52 (4H, m), 3.60-3.74 (1H, m), 3.85-4.05 (2H, m), 4.78-4.92 (1H, m), 7.33-7.46 (5H, m).

Example 15

[Formula 41]

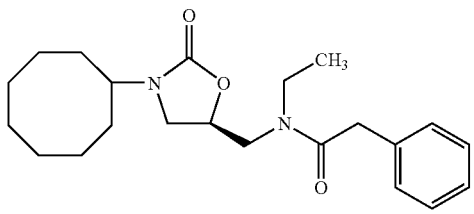

(Compound I-18) yield 83%, 1H-NMR (CDCl3): δ(ppm) 1.13 (3H, t, J=7 Hz), 1.44-1.76 (14H, m), 3.21 (1H, dd, J=9, 7.5 Hz), 3.30 (1H, dd, J=14.5, 6.5 Hz), 3.44-3.58 (3H, m), 3.73 (2H, s), 3.84 (1H, d, J=14.5, 3 Hz), 3.85-3.95 (1H, m), 4.65-4.70 (1H, m), 7.20-7.36 (5H, m).

Example 16

[Formula 42]

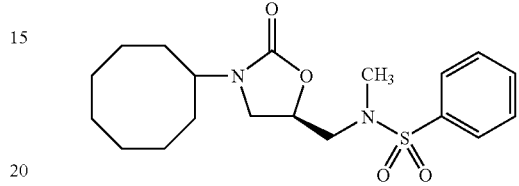

(Compound I-19) yield 68%, 1H-NMR (CDCl3): δ(ppm) 1.50-1.85 (14H, m), 2.86 (3H, s), 3.13 (1H, dd, J=14.5, 4.5 Hz), 3.36 (1H, dd, J=14.5, 5 Hz), 3.62 (2H, d, J=7 Hz), 3.88-4.00 (1H, m), 4.57-4.68 (1H, m), 7.50-7.85 (5H, m).

Example 17

[Formula 43]

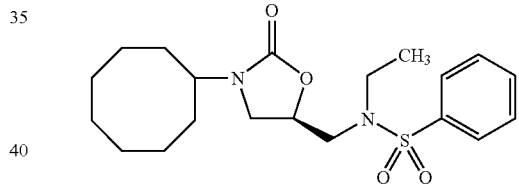

(Compound I-20) yield 68%, 1H-NMR (CDCl3): δ(ppm) 1.11 (3H, t, J=7 Hz), 1.48-1.80 (14H, m), 3.19-3.40 (3H, m), 3.46-3.65 (3H, m), 3.85-3.95 (1H, m), 4.60-4.70 (1H, m), 7.50-7.65 (3H, m), 7.77-7.83 (2H, m).

Example 18

[Formula 44]

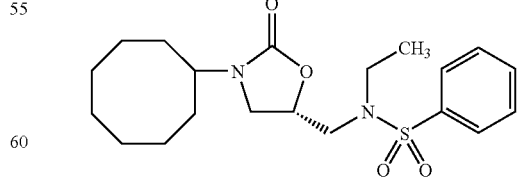

(Compound I-21) yield 71%, 1H-NMR (CDCl3): δ(ppm) 1.11 (3H, t, J=7 Hz), 1.45-1.80 (14H, m), 3.18-3.40 (3H, m), 3.45-3.65 (3H, m), 3.87-4.00 (1H, m), 4.59-4.70 (1H, m), 7.50-7.65 (3H, m), 7.77-7.85 (2H, m).

Example 19

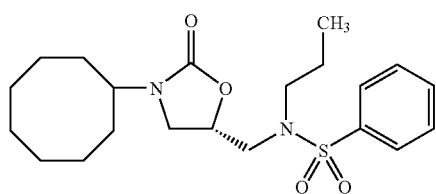
[Formula 45]

(Compound I-22) yield 99%, 1H-NMR (CDCl3): δ(ppm) 0.85 (3H, t, J=7.5 Hz), 1.46-1.80 (16H, m), 2.95-3.12 (1H, m), 3.14-3.22 (2H, m), 3.40-3.64 (3H, m), 3.87-4.00 (1H, m), 4.56-4.70 (1H, m), 7.50-7.65 (3H, m), 7.76-7.85 (2H, m).

Example 20

[Formula 46]
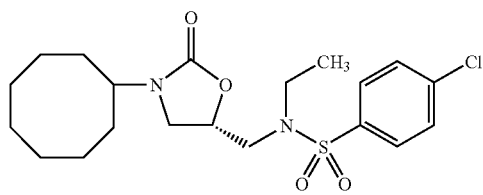

(Compound I-23) yield 77%, 1H-NMR (CDCl3): δ(ppm) 1.12 (3H, t, J=7 Hz), 1.45-1.80 (14H, m), 3.19-3.40 (3H, m), 3.46-3.64 (3H, m), 3.80-4.00 (1H, m), 4.59-4.70 (1H, m), 7.50 (2H, d, J=8.5 Hz), 7.73 (2H, d, J=8.5 Hz).

Example 21

[Formula 47]
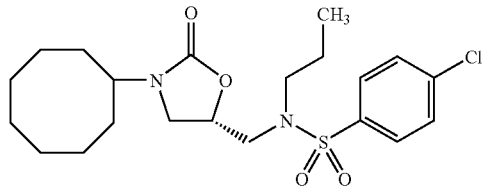

(Compound I-24) yield 85%, 1H-NMR (CDCl3): δ(ppm) 0.86 (3H, t, J=7.5 Hz), 1.46-1.80 (16H, m), 2.98-3.26 (3H, m), 3.45-3.65 (3H, m), 3.87-4.00 (1H, m), 4.57-4.68 (1H, m), 7.52 (2H, d, J=8.5 Hz), 7.73 (2H, d, J=8.5 Hz).

Example 22

[Formula 48]
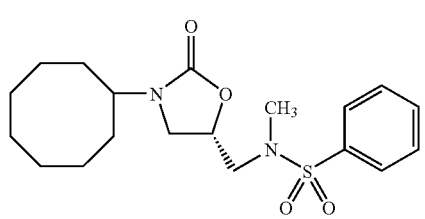

(Compound I-25) yield 76%, 1H-NMR (CDCl3): δ(ppm) 1.47-1.85 (14H, m), 2.86 (3H, s), 3.13 (1H, dd, J=14.5, 4.5 Hz), 3.36 (1H, dd, J=14.5, 5 Hz), 3.62 (2H, d, J=7.5 Hz), 3.88-4.00 (1H, m), 4.58-4.68 (1H, m), 7.52-7.67 (3H, m), 7.74-7.82 (2H, m).

Example 23

[Formula 49]
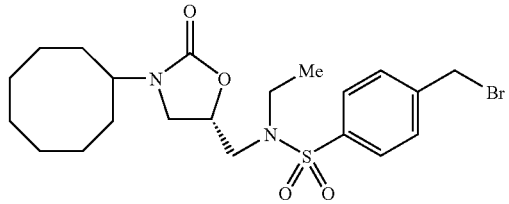

(Compound I-26) yield 57%, 1H-NMR (CDCl3): δ(ppm) 1.13 (3H, t, J=7 Hz), 1.48-1.80 (14H, m), 3.19-3.40 (3H, m), 3.46-3.65 (3H, m), 3.87-4.00 (1H, m), 4.50 (2H, s), 4.60-4.70 (1H, m), 7.55 (2H, d, J=8 Hz), 7.77 (2H, d, J=8 Hz).

Example 24

[Formula 50]
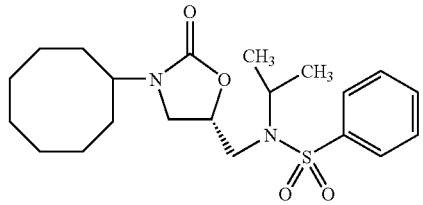

(Compound I-27) yield 46%, 1H-NMR (CDCl3): δ(ppm) 0.97 (3H, d, J=7 Hz), 1.09 (3H, t, J=7 Hz), 1.45-1.85 (14H, m), 3.23 (1H, dd, J=15.5, 5.5 Hz), 3.42 (1H, dd, J=15.5, 6 Hz), 3.54 (1H, dd, J=9, 6 Hz), 3.65 (1H, t, J=9 Hz), 3.90-4.00 (1H, m), 4.03 (1H, t, J=7 Hz), 4.72-4.82 (1H, m), 7.48-7.65 (3H, m), 7.78-7.86 (2H, m).

Example 25

[Formula 51]
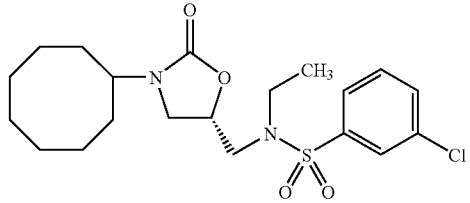

(Compound I-28) yield 59%, 1H-NMR (CDCl3): δ(ppm) 1.14 (3H, t, J=7 Hz), 1.49-1.82 (14H, m), 3.20-3.42 (3H, m), 3.46-3.66 (3H, m), 3.86-4.00 (1H, m), 4.60-4.70 (1H, m), 7.49 (1H, t, J=8 Hz), 7.58 (1H, dt, J=8, 1.5 Hz), 7.63 (1H, dt, J=8, 1.5 Hz), 7.79 (1H, t, J=1.5 Hz).

Example 26

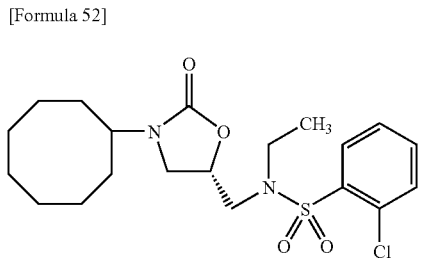

[Formula 52]

(Compound I-29) yield 71%, 1H-NMR (CDCl3): δ(ppm) 1.04 (3H, t, J=7 Hz), 1.45-1.80 (14H, m), 3.30-3.65 (5H, m), 3.83 (1H, dd, J=15.5, 4.5 Hz), 3.89-3.99 (1H, m), 4.60-4.71 (1H, m), 7.38-7.55 (3H, m), 8.09-8.15 (1H, m).

Example 27

[Formula 53]

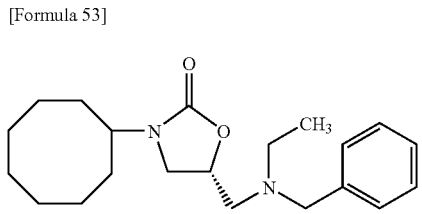

(Compound I-30) yield 52%, 1H-NMR (CDCl3): δ(ppm) 1.08 (3H, t, J=7 Hz), 1.40-1.75 (14H, m), 2.50-2.74 (4H, m), 3.13 (1H, dd, J=8.5, 6 Hz), 3.40 (1H, t, J=8.5 Hz), 3.48 (1H, d, J=13.5 Hz), 3.71 (1H, d, J=13.5 Hz), 3.80-3.90 (1H, m), 4.36-4.48 (1H, m), 7.20-7.42 (5H, m).

Example 28

[Formula 54]

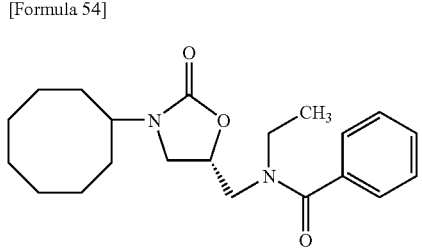

(Compound I-31) yield 99%, 1H-NMR (CDCl3): δ(ppm) 1.09 (3H, t, J=7 Hz), 1.40-1.80 (14H, m), 3.30-3.52 (4H, m), 3.67 (1H, t, J=8.5 Hz), 3.89-4.05 (2H, m), 4.79-4.92 (1H, m), 7.34-7.47 (5H, m).

Example 29

[Formula 55]

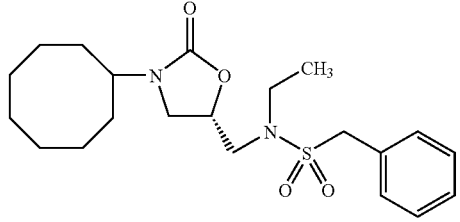

(Compound I-32) yield 87%, 1H-NMR (CDCl3): δ(ppm) 1.18 (3H, t, J=7 Hz), 1.47-1.78 (14H, m), 3.07 (1H, dd, J=15, 6.5 Hz), 3.14-3.33 (4H, m), 3.43 (1H, t, J=9 Hz), 3.82-3.96 (1H, m), 4.29 (2H, s), 4.30-4.38 (1H, m), 7.39 (5H, s).

Example 30

[Formula 56]

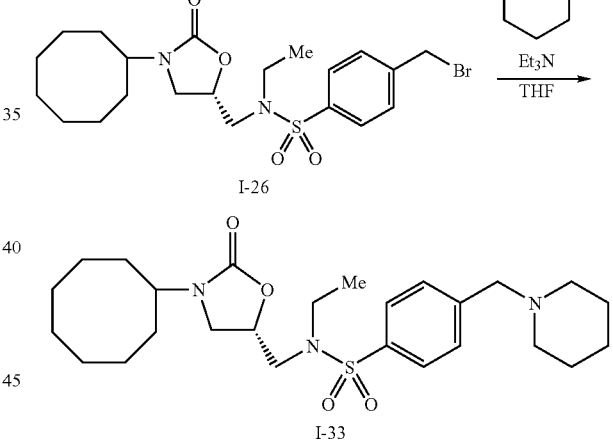

A mixture of 0.16 g (0.3282 mmol) of Compound I-26, 31 mg (0.3610 mmol) of piperazine, 37 mg (0.3610 mmol) of triethylamine and 1 mL of anhydrous tetrahydrofuran was stirred for 15 hours at room temperature. After extraction by adding water and ethyl acetate to the reaction solution, the organic layer was adjusted to pH=3 by 2N-hydrochloric acid aqueous solution and extracted, and then the aqueous layer was adjusted to pH=9 by 2N-sodium hydroxide, and extracted with ethyl acetate. The organic layer was washed with saturated saline, and dried with sodium sulfate. The solvent was removed under reduced pressure, to obtain 0.18 g (100%) (I-33) of a colorless liquid.

1H-NMR (CDCl3): δ(ppm) 1.12 (3H, t, J=7 Hz), 1.40-1.80 (20H, m), 2.32-2.42 (4H, m), 3.16-3.37 (3H, m), 3.45-3.52 (1H, m), 3.52 (2H, s), 3.55-3.62 (2H, m), 3.86-3.98 (1H, m), 4.59-4.70 (1H, m), 7.49 (2H, d, J=8.5 Hz), 7.72 (2H, d, J=8.5 Hz).

The compounds shown below were synthesized in a similar manner.

Example 31

[Formula 57]

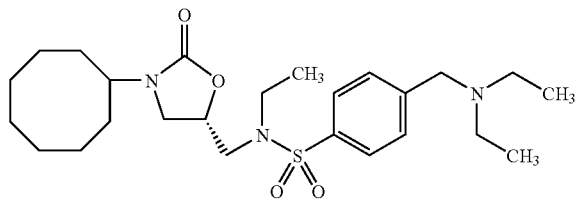

(I-34) yield 36%, 1H-NMR (CDCl3): δ(ppm) 1.03 (6H, t, J=7 Hz), 1.11 (3H, t, J=7 Hz), 1.47-1.80 (14H, m), 2.52 (4H, q, J=7 Hz), 3.16-3.39 (3H, m), 3.50 (1H, dd, J=15, 5.5 Hz), 3.58-3.61 (2H, m), 3.62 (2H, s), 3.85-4.00 (1H, m), 4.59-4.70 (1H, m), 7.51 (2H, d, J=8 Hz), 7.74 (2H, d, J=8 Hz).

Example 32

[Formula 58]

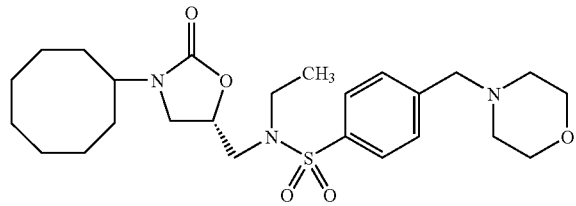

(I-35) yield 39%, 1H-NMR (CDCl3): δ(ppm) 1.12 (3H, t, J=7 Hz), 1.50-1.80 (14H, m), 2.45 (4H, t, J=4.5 Hz), 3.17-3.40 (3H, m), 3.51 (1H, dd, J=15, 5.5 Hz), 3.56 (2H, s), 3.57-3.65 (2H, m), 3.72 (4H, t, J=~4.5 Hz), 3.88-3.98 (1H, m), 4.60-4.70 (1H, m), 7.51 (2H, d, J=8.5 Hz), 7.74 (2H, d, J=8.5 Hz).

Example 33

[Formula 59]

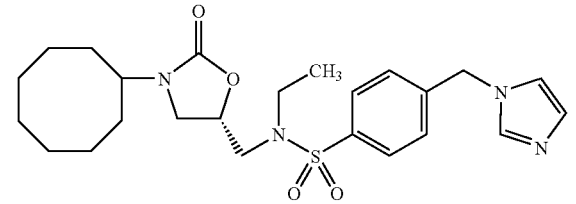

(I-36) yield 41%, 1H-NMR (CDCl3): δ(ppm) 1.12 (3H, t, J=7 Hz), 1.48-1.80 (14H, m), 3.16-3.40 (3H, m), 3.45-3.66 (3H, m), 3.86-3.99 (1H, m), 4.59-4.70 (1H, m), 5.23 (2H, s), 6.92 (1H, s), 7.15 (1H, s), 7.26 (2H, d, J=8.5 Hz), 7.58 (1H, s), 7.79 (2H, d, J=8.5 Hz).

Example 34

[Formula 60]

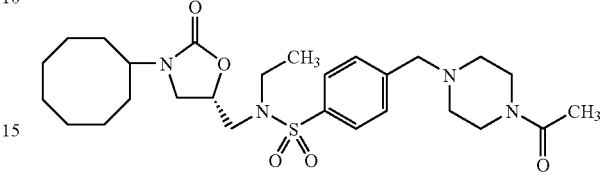

(I-37) yield 87%, 1H-NMR (CDCl3): δ(ppm) 1.12 (3H, t, J=7 Hz), 1.45-1.80 (14H, m), 2.09 (3H, s), 2.35-2.50 (4H, m), 3.15-3.40 (3H, m), 3.42-3.50 (4H, m), 3.52-3.68 (5H, m), 3.88-4.00 (1H, m), 4.60-4.73 (1H, m), 7.50 (2H, d, J=8.5 Hz), 7.75 (2H, d, J=8.5 Hz).

Example 35

[Formula 61]

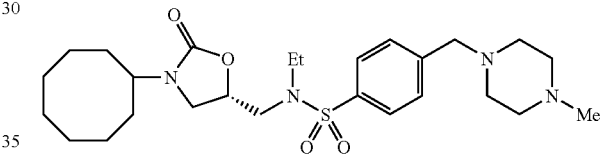

(I-38) yield 78%, 1H-NMR (CDCl3): δ(ppm) 1.12 (3H, t, J=7 Hz), 1.45-1.80 (14H, m), 2.30 (3H, s), 2.48 (8H, brs), 3.15-3.40 (3H, m), 3.45-3.67 (5H, m), 3.85-4.00 (1H, m), 4.60-4.70 (1H, m), 7.50 (2H, d, J=8 Hz), 7.75 (2H, d, J=8 Hz).

Test Example 1

Evaluation Method of 11β-HSD1 Inhibitor

Evaluation of Compound Against Human 11β-HSD1

After preincubating an inhibitor in a reaction solution consisting of 50 mM sodium phosphate buffer (pH 7.6), bovine serum albumin (1 mg/mL), NADPH (0.42 mg/mL), glucose-6-phosphate (1.26 mg/mL), glucose-6-phosphate dehydrogenase and an enzyme at room temperature for 30 minutes, cortisone (5 μM) which is a substrate was added (total amount 10 μL). After reacting at 37° C. for 2 hours, an XL-665-labeled cortisol solution (5 μL), and a Cryptate-labeled anti-cortisol antibody solution (5 μL) were added, a reaction was performed at room temperature for 2 hours, and fluorescence intensity (HTRF method) was measured. A cortisol concentration was measured from a standard curve prepared using a known concentration of cortisol for each assay.

Taking a concentration of cortisol generated in the absence of the inhibitor as a control value, 50% inhibition concentration (IC50 value) of the inhibitor against 11β-HSD1 was calculated from an inhibition curve plotting inhibition rate against the control value at each concentration of an inhibitor.

Test Example 2

Evaluation Method of 11β-HSD1 Inhibitor

Evaluation of Compound Against Mouse 11β-HSD1

After preincubating an inhibitor in a reaction solution consisting of 50 mM sodium phosphate buffer (pH 7.6), bovine serum albumin (1 mg/mL), NADPH (0.42 mg/mL), glucose-6-phosphate (1.26 mg/mL), glucose-6-phosphate dehydrogenase, and an enzyme at room temperature for 30 minutes, 11-dehydrocorticosterone (2 μM) which is a substrate was added (total amount 10 μL). After reacting at 37° C. for 2 hours, an XL-665-labeled cortisol solution (5 μL), and a Cryptate-labeled anti-cortisol antibody solution (5 μL) were added, a reaction was performed at room temperature for 2 hours, and fluorescence intensity (HTRF method) was measured.

A corticosterone concentration was measured from a standard curve prepared using a known concentration of corticosterone for each assay.

Taking a concentration of corticosterone generated in the absence of the inhibitor as a control value, 50% inhibition concentration (IC50 value) of the inhibitor against 11β-HSD1 was calculated from an inhibition curve plotting inhibition rate against the control value at each concentration of the inhibitor.

Results of Test Examples 1 and 2 are shown below.
Compound I-21: human $IC_{50}$=0.43 μM, mouse $IC_{50}$=8.4 μM Test Example 3

Material and Method of Oral Absorption of 11β-HSD1 Inhibitor Against Diabetes (1) Animal: male C57BL/6J Jcl mice at the age of 6 weeks were purchased from CLEA Japan, Inc., and used for the experiment at the age of 7 weeks after preliminary rearing for 1 week.
(2) Rearing conditions: Mice are fed in the following environment: temperature 23±2° C., humidity 55±10%, in a cycle of 8:00 to 20:00 in light and 20:00 to 8:00 in dark. During preliminary rearing, and a test term, the mice were allowed to liberally intake solid feed (CE-2, CLEA Japan, Inc.) and sterilized tap water.
(3) Identification of individual and cage: Individual number was written with oil ink on the tail of a mouse to achieve identification. A cage was attached with a label describing a name of a person in charge of the test, data of arrival, a strain, a sex, and a name of a supplier, and fed by 20 mice/cage during preliminary rearing. After start of the experiment, mice were fed in 3 mice/cage.
(4) Setting of dose and grouping: The following groups were set according to dose amounts of oral administration and intravenous administration.
  Oral administration 20 mg/kg (n=3)
  Intravenous administration 5 mg/kg (n=3)
(5) Preparation of administration liquid: A preparation method is shown below. A suspension was prepared using 0.5% methylcellulose (1500 cP) as a medium for oral administration. A solubilized solution was prepared using N,N-dimethylacetamide/polyethylene glycol 400(=½) as a medium for intravenous administration.
(6) Administration method: As to oral administration, the dosing suspension was administered compulsorily into the stomach by means of an oral sonde at a rate of 10 mL/kg. As to intravenous administration, the dosing solution was administered into caudal vein at a rate of 2.5 mL/kg by means of a glass syringe.
(7) End point: Blood was collected from heart by time-point blood sampling, and a drug concentration in plasma was measured by using HPLC or LC/MS/MS.
(8) Statistical analysis: As to transition of a plasma concentration, an area under a plasma concentration-time curve (AUC) was calculated by using non-linear minimum program WinNonlin (registered trade name), and bioavailability was calculated from AUCs of the oral administration group and the intravenous administration group.

FORMULATION EXAMPLES

The following Formulation Examples 1 to 8 are merely examples, and are not intended to limit the scope of the present invention. The term "active ingredient" means the present compound, its tautomer, prodrug thereof, pharmaceutically acceptable salt thereof, or hydrate thereof.

Formulation Example 1

A hard gelatin capsule is prepared by using the following ingredients:

|  | Dose (mg/capsule) |
| --- | --- |
| Active ingredient | 250 |
| Starch (dry) | 200 |
| Magnesium stearate | 10 |
| Total | 460 mg |

Formulation Example 2

A tablet is prepared by using the following ingredients:

|  | Dose (mg/tablet) |
| --- | --- |
| Active ingredient | 250 |
| Cellulose (microcrystal) | 400 |
| Silicon dioxide (fumed) | 10 |
| Stearic acid | 5 |
| Total | 665 mg |

The ingredients are mixed, and compressed to form tables each weighing 665 mg.

Formulation Example 3

An aerosol solution containing the following ingredients is prepared:

|  | Weight |
| --- | --- |
| Active ingredient | 0.25 |
| Ethanol | 25.75 |
| Propellant 22 (chlorodifluoromethane) | 74.00 |
| Total | 100.00 |

The active ingredient and ethanol are mixed, and the mixture is added to part of propellant 22, cooled to −30° C., and transferred to a packing machine. Then, a necessary amount is supplied to a stainless steel container, and diluted with the remaining propellant. A bubble unit is attached to the container.

Formulation Example 4

A tablet containing 60 mg of the active ingredient is prepared in the following manner:

| | |
|---|---|
| Active ingredient | 60 mg |
| Starch | 45 mg |
| Microcrystalline cellulose | 35 mg |
| Polyvinylpyrrolidone (10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. An aqueous solution containing polyvinylpyrrolidone is mixed with obtained powder and then the mixture is passed through a No. 14 mesh U.S. sieve. Granules obtained in this manner are dried at 50° C. and passed through a No. 18 mesh U.S. sieve. The sodium carboxymethyl starch, magnesium stearate and talc that are passed through a No. 60 mesh U.S. sieve in advance, are added to the granules, mixed, and then compressed by a tableting machine to obtain tablets each weighing 150 mg.

Formulation Example 5

A capsule containing 80 mg of the active ingredient is prepared in the following manner:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, starch, cellulose, and magnesium stearate are mixed, and passed through a No. 45 mesh U.S. sieve, and filled into a hard gelatin capsule in 200 mg quantities.

Formulation Example 6

Suppository containing 225 mg of the active ingredient is prepared in the following manner:

| | |
|---|---|
| Active ingredient | 225 mg |
| Saturated fatty acid glyceride | 2000 mg |
| Total | 2225 mg |

The active ingredient is passed through a No. 60 mesh U.S. sieve, and suspended in saturated fatty acid glyceride that is melted by heating least necessarily in advance. Then, the resultant mixture is put into an apparent 2 g mold, and cooled.

Formulation Example 7

A suspension containing 50 mg of the active ingredient is prepared in the following manner:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Pigment | q.v. |
| Purified water to total | 5 mL |

The active ingredient is passed through a No. 45 mesh U.S. sieve, and mixed with sodium carboxymethyl cellulose and syrup to form a smooth paste. The benzoic acid solution and the flavor diluted with part of water are added, and stirred. Then a sufficient amount of water is added to achieve required volume.

Formulation Example 8

| An intravenous formulation is prepared in the following manner: | |
|---|---|
| Active ingredient | 100 mg |
| Saturated fatty acid glyceride | 1000 mL |

The solution of the above ingredients is intravenously administered to a patient usually at a speed of 1 mL per minute.

INDUSTRIAL APPLICABILITY

As is apparent from the above test examples, the compounds according to the present invention show inhibitory activity on 11β-hydroxysteroid dehydrogenase type 1. Therefore, the compounds according to the present invention are very useful as therapeutic agents for diabetes.

The invention claimed is:

1. A method for treating a 11β-hydroxysteroid dehydrogenase type 1 related disease, comprising administering to a subject an effective amount of a compound represented by the Formula (I):

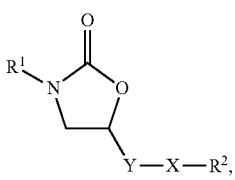

or its pharmaceutically acceptable salt,
wherein $R^1$ is optionally substituted cycloalkyl, optionally substituted cycloalkylalkyl, optionally substituted non-aromatic heterocycle or optionally substituted non-aromatic heterocyclealkyl,
X is —O—, —$NR^3$—, —$NR^3C(=O)$— or —$NR^3S(=O)_2$—, $R^2$ is optionally substituted aryl, optionally substituted arylalkyl, optionally substituted cycloalkyl, optionally substituted cycloalkylalkyl, optionally substituted heteroaryl, optionally substituted heteroarylalkyl, optionally substituted heterocycle or optionally substituted heterocyclealkyl, $R^3$ is hydrogen or optionally substituted alkyl, Y is —$(CR^4R^5)n$-, $R^4$ and $R^5$ are each independently hydrogen, optionally substituted alkyl, halogen or hydroxy, and n is an integer of 1 to 6, wherein the 11β-hydroxysteroid dehydrogenase type 1 related disease is at least one selected from the group consisting of hyperlipidemia, diabetes, obesity, arteriosclerosis, atherosclerosis, hyperglycemia and syndrome X.

2. The method according to claim 1, wherein n is 1, and $R^4$ and $R^5$ are hydrogen.

3. The method according to claim 2, wherein $R^1$ is optionally substituted cycloalkyl, optionally substituted cycloalkylalkyl, optionally substituted non-aromatic heterocycle or optionally substituted non-aromatic heterocyclealkyl.

4. The method according to claim 1, wherein the disease is diabetes.

* * * * *